(12) United States Patent
Goodreau et al.

(10) Patent No.: US 11,532,379 B2
(45) Date of Patent: Dec. 20, 2022

(54) METHODS AND SYSTEMS OF TRACKING DISEASE CARRYING ARTHROPODS

(71) Applicant: THE LIVLYME FOUNDATION, Denver, CO (US)

(72) Inventors: Olivia Newell Goodreau, Denver, CO (US); Holiday Grogan Goodreau, Denver, CO (US); Matthew S. Fox, Marion, OH (US); Jeffrey A. Stauffer, Columbus, OH (US); Sean P. Cowan, Columbus, OH (US); Gregory J. Maddox, Powell, OH (US); Wilson P. Bridgett, Hilliard, OH (US); Stephanie A. Perkins, Lewis Center, OH (US)

(73) Assignee: THE LIVLYME FOUNDATION, Denver, CO (US)

( * ) Notice: Subject to any disclaimer, the term of this patent is extended or adjusted under 35 U.S.C. 154(b) by 537 days.

(21) Appl. No.: 16/277,332

(22) Filed: Feb. 15, 2019

(65) Prior Publication Data
US 2019/0259472 A1 Aug. 22, 2019

Related U.S. Application Data

(60) Provisional application No. 62/710,462, filed on Feb. 16, 2018.

(51) Int. Cl.
| | | |
|---|---|---|
| *G01N 33/48* | (2006.01) | |
| *G16B 45/00* | (2019.01) | |
| *G16B 5/00* | (2019.01) | |
| *G16H 50/30* | (2018.01) | |
| *G16B 50/00* | (2019.01) | |
| *G16B 10/00* | (2019.01) | |
| *G16B 40/00* | (2019.01) | |

(52) U.S. Cl.
CPC .............. *G16B 45/00* (2019.02); *G16B 5/00* (2019.02); *G16B 10/00* (2019.02); *G16B 40/00* (2019.02); *G16B 50/00* (2019.02); *G16H 50/30* (2018.01)

(58) Field of Classification Search
None
See application file for complete search history.

(56) References Cited

U.S. PATENT DOCUMENTS

| 9,563,852 | B1 | 2/2017 | Wiles et al. | |
|---|---|---|---|---|
| 2005/0025357 | A1* | 2/2005 | Landwehr | A01M 1/026 382/170 |
| 2008/0007397 | A1* | 1/2008 | Glazer | G08B 27/008 340/539.11 |
| 2014/0071276 | A1* | 3/2014 | Seifer | G08C 17/02 340/870.01 |
| 2014/0244344 | A1* | 8/2014 | Bilet | G06Q 10/0635 705/7.28 |
| 2016/0061625 | A1* | 3/2016 | Wang | G06Q 30/0214 701/454 |
| 2016/0110984 | A1 | 4/2016 | Seol | |

OTHER PUBLICATIONS

International Preliminary Report on Patentability for International Application No. PCT/US2019/018229, dated Aug. 27, 2020.
Antonise-Kamp, L., et al. "Prevention of Tick Bites: An Evaluation of a Smartphone App" BMC Infectious Diseases; 2017.
International Search Report for International Application No. PCT/US2019/018229, dated Apr. 29, 2019.
Written Opinion for International Application No. PCT/US2019/018229, dated Apr. 29, 2019.

\* cited by examiner

*Primary Examiner* — Anna Skibinsky
(74) *Attorney, Agent, or Firm* — Sheridan Ross, PC

(57) ABSTRACT

The present invention comprises the capture and display of arthropod, human and arthropod-based metadata, which is capable of tracking and displaying the metadata, which is time and location-based, in order to show migration paths of arthropods and/or the diseases they have the potential to carry. This real-time view can help predict future arthropod and disease based on various scenarios such as, but not limited to: increased exposure based on the following: a user's geo-location, date and/or time of year, carrier type, etc. These variables can then assist with the education, awareness and potential prevention of disease.

20 Claims, 27 Drawing Sheets

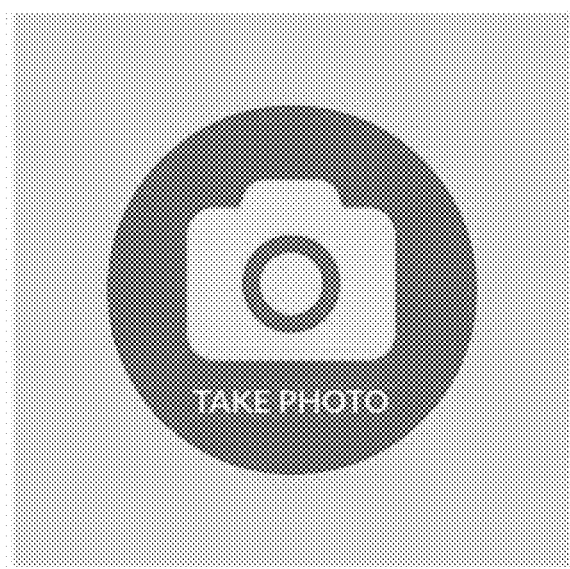
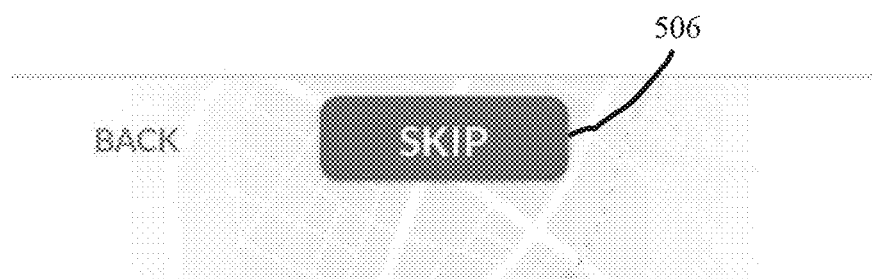
FIG. 5

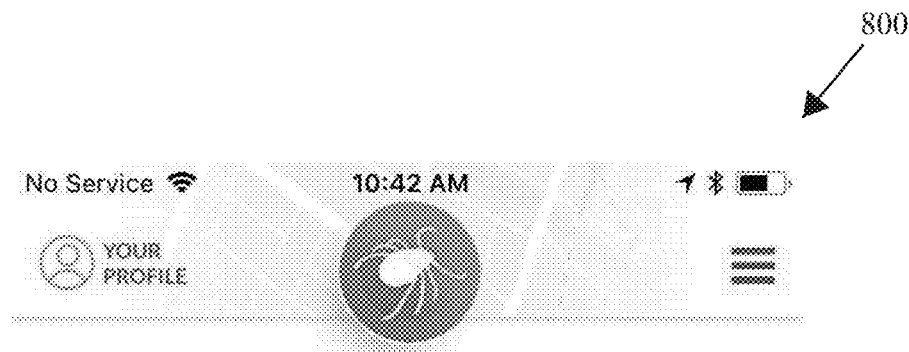

Step 1 of 7: Remove Tick

The most important thing to do is to remove the tick from the carrier's body. Follow the instructions below to safely remove the tick.

Please do not dispose of the removed tick permanently. We ask that you consider submitting the tick for testing for Lyme disease. We provide instructions on the following screens on how to do so with validated testing labs.

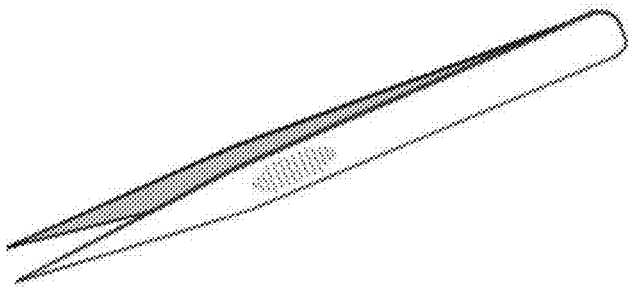

Pointed tweezers are best for removing ticks. Blunt tweezers can tear the tick and squeeze germs into the bite area.

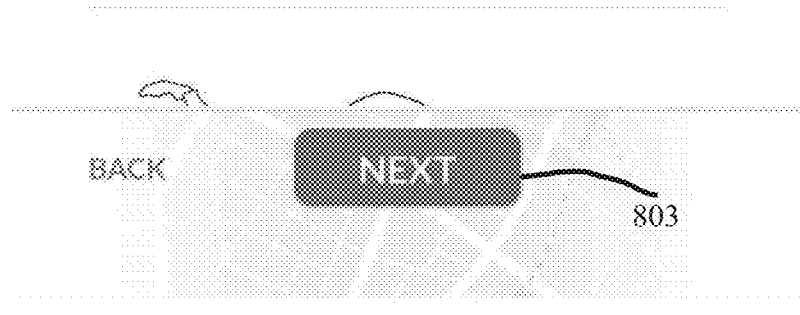

FIG. 8

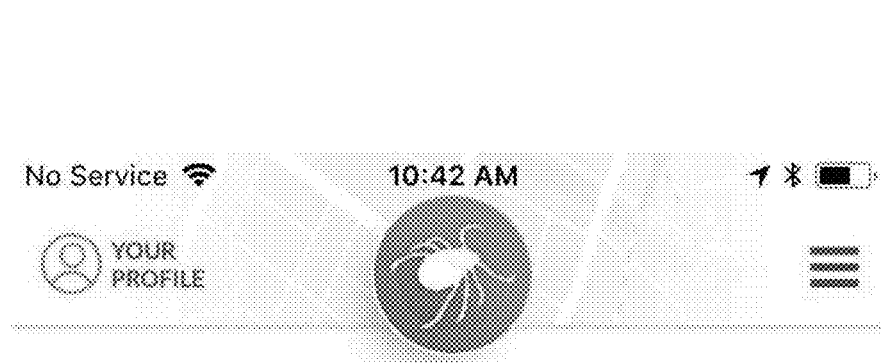
Step 2 of 7: Identify Tick
Tap the ticks below to get information about each tick species and identify what type of tick bite you are reporting.
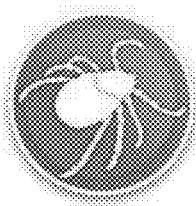 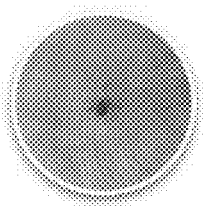 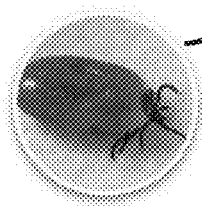
Can not Identify | Can not Identify: Poppyseed Ticks | Can not Identify: Engorged Ticks
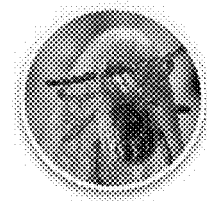 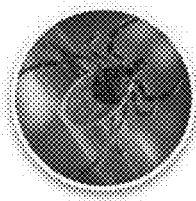 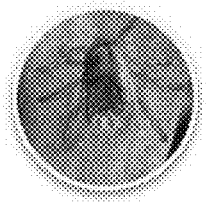
American Dog Tick | Blacklegged Tick | Brown Dog Tick
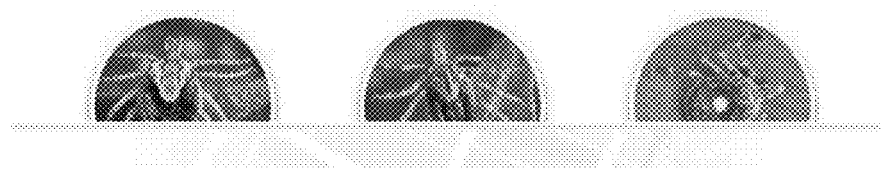
BACK
FIG. 9A

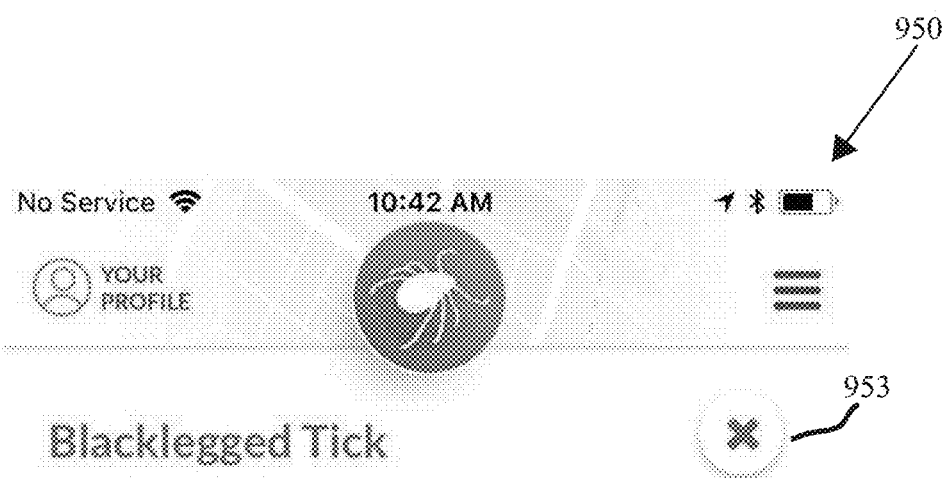
Blacklegged Tick
Scientific Name: *Ixodes scapularis*
Known Location(s):
- Northeastern United States
- Upper midwestern United States
FIG. 9B 1700
No Service 📶     10:53 AM     ➤ ✱ 🔋
<     Main Menu
 Tick Protection Tips
 Tickbourne Disease Resources
 Testing and Labs
 Share TickTracker
 Donate Now
 Rate Us
 About TickTracker
 TickTockBoom Game
 Contact Us
 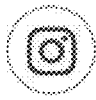 
Privacy Policy     Terms Of Use
FIG. 17

METHODS AND SYSTEMS OF TRACKING DISEASE CARRYING ARTHROPODS

CROSS REFERENCE TO RELATED APPLICATIONS

The present application claims the benefits of and priority, under 35 U.S.C. § 119(e), to U.S. Provisional Application Ser. No. 62/710,462, filed Feb. 16, 2018, entitled "TRACKING APPLIANCE, AND IN PARTICULAR AN ARTHROPOD TRACKING TOOL AND ASSOCIATED APP." The entire disclosures of the application listed above is hereby incorporated by reference, in its entirety, for all that they teach and for all purposes.

FIELD

The present disclosure relates generally to a mobile tracking application and more particularly to an application capable of tracking the location and date of an identified arthropod (e.g. a tick) to create a prevalence indicator of various arthropod types (e.g. ticks) within a real-time defined geo-location.

BACKGROUND

Disease and infections cause a great number of problems throughout society. The unpredictability of the causes of disease and infection prevents adequate response to outbreaks.

For example, some diseases and infections are carried by arthropods. The presence of disease and/or infection carrying arthropods is a difficult and sometimes nearly impossible factor for medical professionals to ascertain.

This difficulty is particularly evident in the case of disease and/or infection carrying arthropods such as ticks. Whether a particular area is infested with disease and/or infection carrying ticks is impossible for a human to determine without extreme efforts.

Conventional methods of locating disease and/or infection carrying arthropods rely on historical data, season and weather data, and estimations. These data sources and estimates are inadequate for properly ascertaining the severity of the risk of infection for a given area. This problem is multiplied by the fact that arthropods migrate from location to location. Meanwhile, the ability for people to enjoy the outdoors without excessive risk of infectious disease is critical for society. Minimizing this risk requires providing adequate notice to those seeking an outdoor experience. However, contemporary methods of spreading the word of ticks and disease relies on inefficient and inaccurate system of word of mouth. A person bit by a tick may or may not know exactly what type of tick it was and may or may not recall exactly where the bite occurred when he or she is reporting it hours or days later.

Because of the constantly changing migration of disease and/or infection carrying arthropods such as ticks, and because contemporary methods of spreading notice are inadequate, what is needed is a way to track the location of disease carrying arthropods which can provide real-time, fact-based analysis of the risk of disease and/or infection-carrying arthropods for a specific area.

BRIEF DESCRIPTION OF THE DRAWINGS

Some embodiments of the present invention are illustrated as an example and are not limited by the figures of the accompanying images, in which like references may indicate similar elements and in which:

FIG. 5 illustrates a user interface allowing a user to take a picture to collect an image of the arthropod in accordance with one or more embodiments as described herein;

FIG. 8 illustrates a user interface providing instructions on how to remove an arthropod that has bitten a human or arthropod in accordance with one or more embodiments as described herein;

FIGS. 9A and 9B illustrates user interfaces providing a user an ability to select which arthropod was responsible for the biting and wish to catalog in accordance with one or more embodiments as described herein;

FIG. 17 illustrates a user interface providing various content related sections of an application to supplement the education and experience of a user to assist with initial and ongoing education and awareness of that arthropod and/or the potential pathogens or diseases it may carry in accordance with one or more embodiments as described herein;

DETAILED DESCRIPTION

Figure 1A:
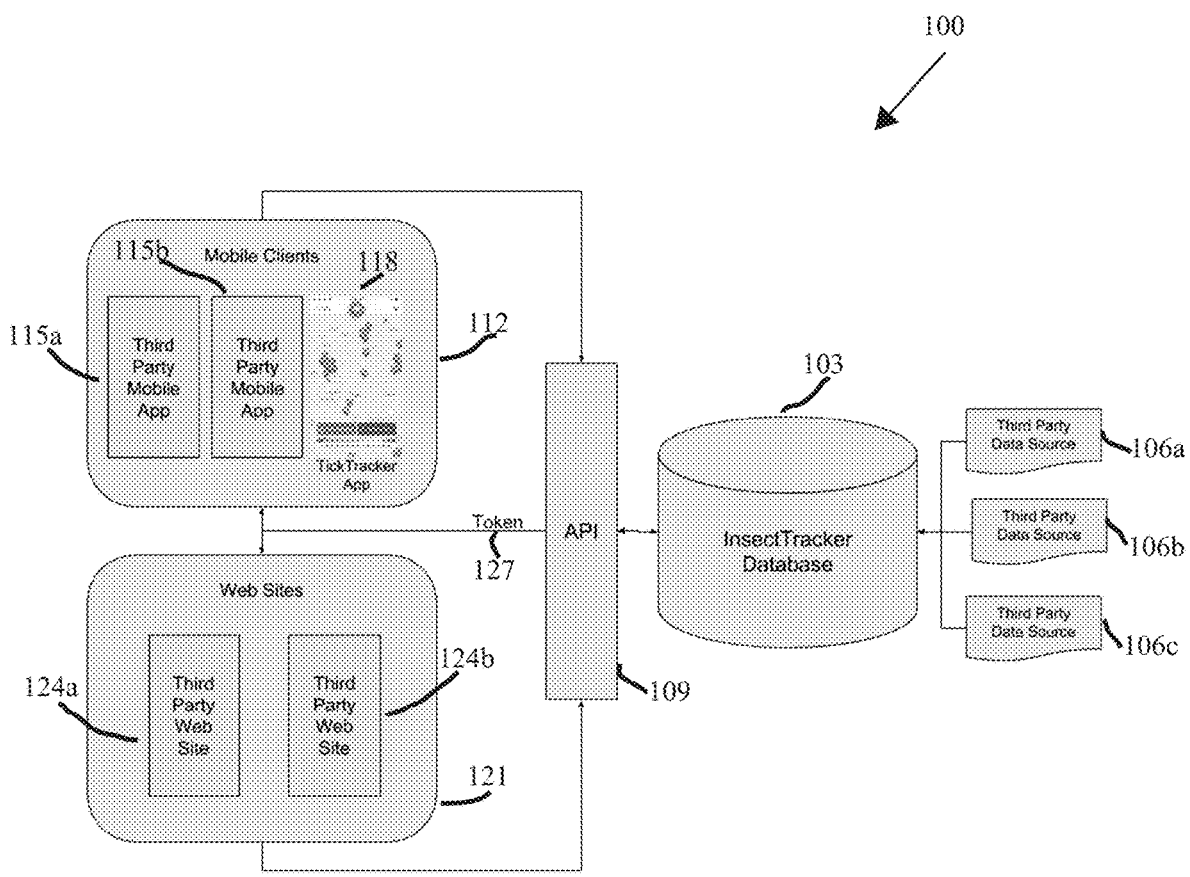
FIG. 1A illustrates a computer system in accordance with one or more embodiments as described herein.

In some embodiments, the core arthropod-tracking technology may be based on data input and aggregation from various sources. The data may be grounded in human verification of an arthropod sighting, biting, and/or sighting or biting vent based on arthropod type, date and time of said event, geo-location of said event, potential disease associated with the arthropod captured from the event, potential carrier type and potential physical location of arthropod biting on carrier. This aggregated data is then transformed to either display or relay the data captured around an arthropod sighting and/or bighting event, with the overall intent to demonstrate real-time arthropod location and migration patterns, which may or may not be associated with potential pathogens or diseases the arthropod may carry. The disclosed systems and methods may be based an API technology and may be able to be embedded within a core mobile application or distributed and consumed by third-party subscribers.

The system may be divided into three main parts: a database, an API application, and one or more applications and websites which consume and send data to the API application.

The database may store records related to arthropod bites and may be able to be loaded with third-party arthropod records via an import script.

The API application may be an MVC (Model, View, Controller) application that resides on a web server that is accessible from the internet. The API application may read data from the database as well as writes new entries back to the database. The API application may include functions capable of storing and retrieving tick bite records and of generating a bite-risk-value based on the current location of a user and the amount of arthropods that are within a certain radius.

The one or more applications and websites may be capable of reading and sending data to and from the API application using REST requests.

The database may be updated with new metadata associated with each record.

The API application may comprise a visual augmented reality (AR) viewer that utilizes a mobile device's camera and geo-location to view data visually via a real-time optical view.

The API application may comprise a heatmap viewer in which data clusters are represented utilizing coloring scheme based on our risk index.

The API application may comprise one or more map filters providing users an ability to filter the maps based on date, data source, tick species.

The API application may comprise real-time notifications which may be presented to users. The real-time notifications may be based on, for example: area exposure (alerts users of the exposure risk within the area they are currently located); current reports (alerts users of most recent (within set parameters of user preference) ticks reported in their area); and areas visited (alerts users of most recent reports (within set parameters of user's preference) of ticks reported in areas the user recently visited).

The API application may comprise a visual artificial intelligence (AI) identifier that may utilize a mobile device's camera to upload images to a server-based application which may analyze the image to assist with identification of the image (tick or other arthropod) and/or tick species.

As illustrated in FIG. 1A, a system 100 for collecting and tracking information relating to arthropods may comprise a database 103. The database 103 may be in communication with one or more third party data sources 106a-c. The database 103 may also be in communication with an API 109 such as a Web API. The API 109 may be accessed by or in communication with one or more mobile clients 112 and/or websites 121. Mobile clients 112 and/or websites 121 may be assigned an API token 127 as a unique identifier of the application requesting access to the API 109. A mobile client 112 may comprise a user device executing one or more third party mobile applications 115a, 115b, and/or a specific application such as a TickTracker App 118. Similarly, a website 121 may comprise one or more third party websites 124a, 124b or a specific website such as a TickTracker website.

For example, a user of a mobile client 112 such as a smartphone may execute an application such as a TickTracker App 118. The application may be capable of receiving information from a database such as an Arthropod-Tracker Database 103.

Figure 1B:
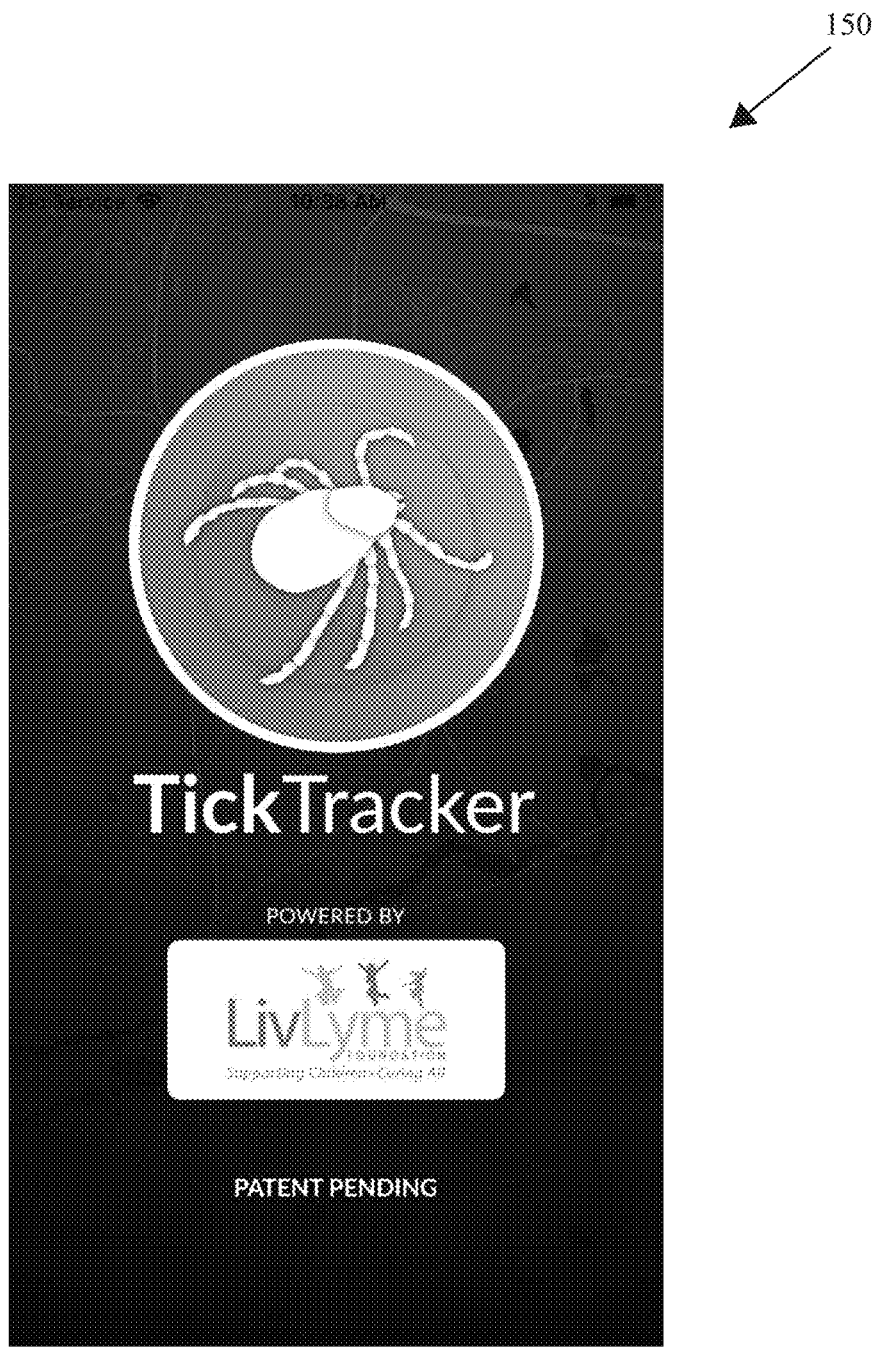
FIG. 1B illustrates the launch screen of an application in accordance with one or more embodiments as described herein.

Upon executing the application, the mobile client 112 may present a loading screen 150 as illustrated in FIG. 1B.

Figure 2:
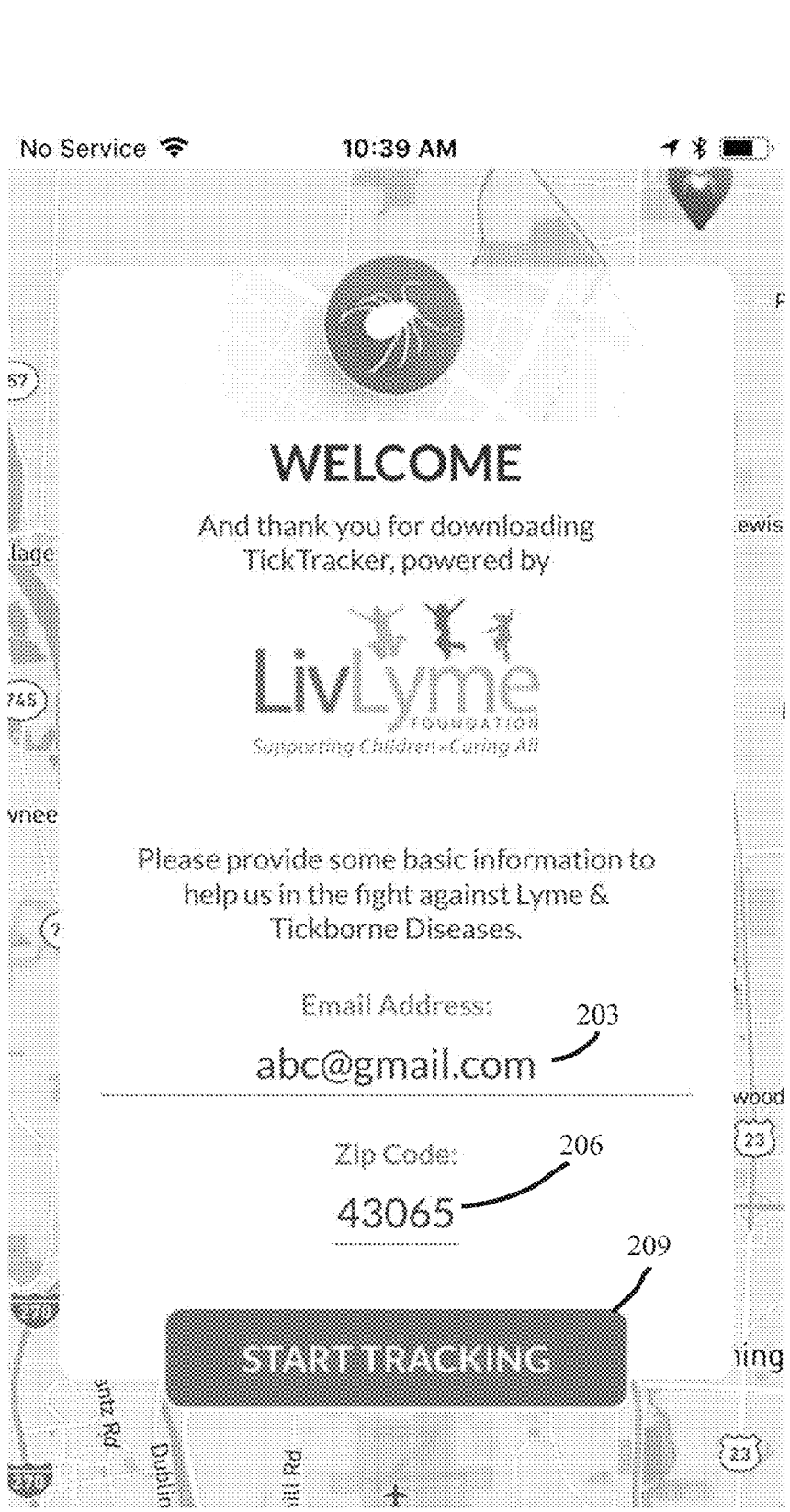
FIG. 2 illustrates a profile collection screen of an application that collects initial contact data along with initial location in accordance with one or more embodiments as described herein.

As illustrated in FIG. 2, the application executing on the mobile client 112 may display a user interface 200 enabling the user to enter contact information in a contact information text field 203 and/or location information in a location information text field 206. In some embodiments, the user may log in to the application and may have a specific user ID and/or password. The user interface 200 may have a button 209 allowing a user to instruct the application to begin tracking.

Figure 3:
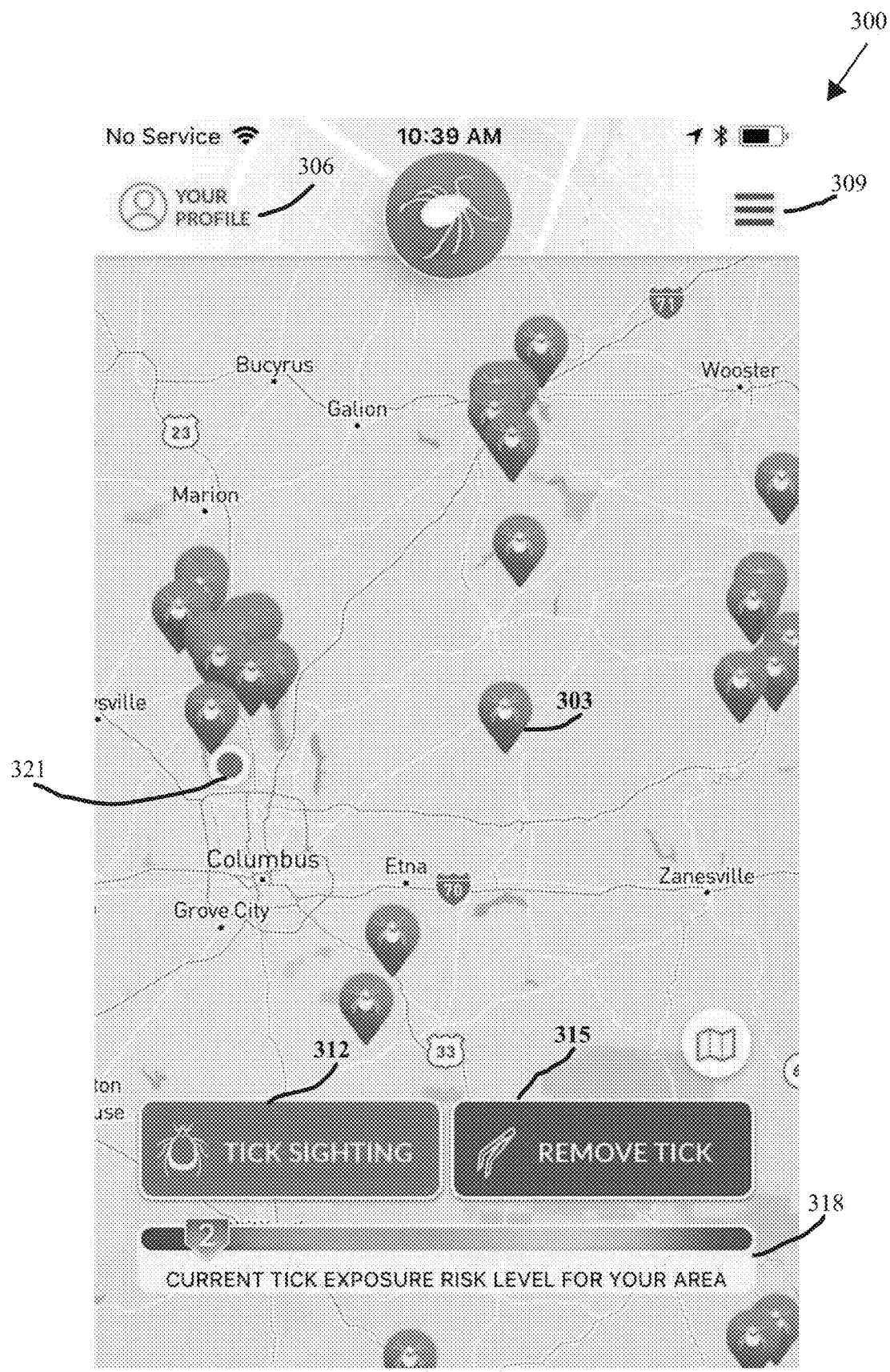
FIG. 3 illustrates a geo-location allowing for geo-location based on a mobile provider in accordance with one or more embodiments as described herein.

As illustrated in FIG. 3, the application executing on the mobile client 112 may display a user interface 300 showing a map with entries 303 of one or more identified arthropod locations in relation to the user's own location 321. The user's location 321 may be automatically determined by the application or another application executing on the mobile client 112 or may be entered manually by the user. The user interface 300 may also comprise user interface buttons allowing access to profile information 306, a menu 309, tick sighting function 312 and/or a remove tick function 315. The user interface 300 may further comprise an indication 318 of a current tick exposure risk level for the area surrounding the user's location 321. In some embodiments, the location used by the application may be a location other than the user's location. For example, the user may enter a different location to ascertain that location's current tick exposure risk level.

Figure 4:
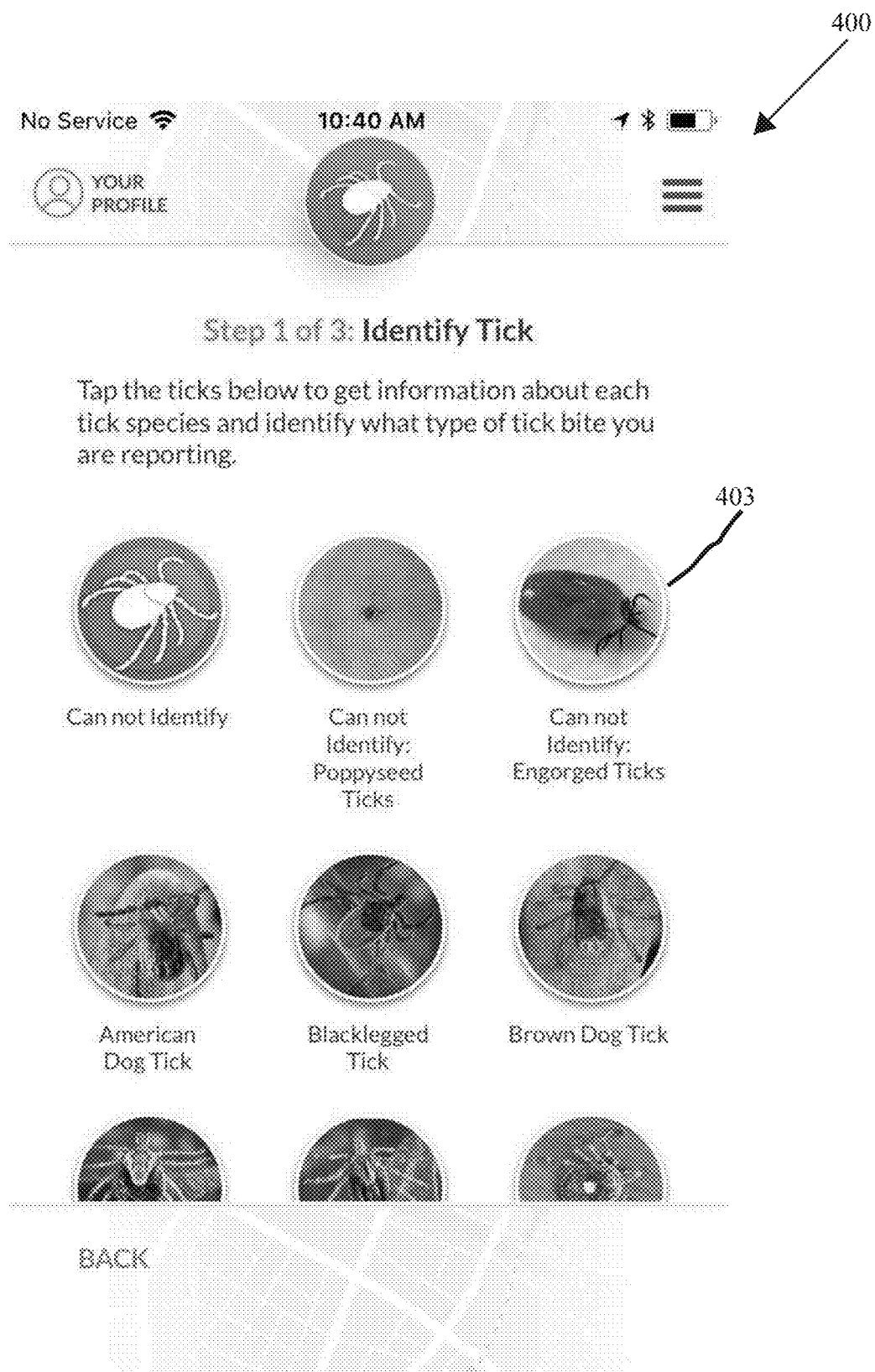
FIG. 4 illustrates a user interface allowing a user to select which arthropod they sighted and wish to catalog in accordance with one or more embodiments as described herein.

If a user of a mobile client 112 executing the application selects a tick sighting function button 312, the mobile client 112 may begin to execute a tick sighting function and the user may be presented with an identify tick selection screen 400 as illustrated in FIG. 4.

An identify tick selection screen 400 may comprise illustrative drawings 403 or photographs of ticks and/or other arthropods. The illustrative drawings 403 may be aimed at helping an uninformed user of the application to identify the type of tick found in the wild. Each illustrative drawing may be of a specific type of tick or arthropod or may comprise a "cannot identify" selection option. Each illustrative drawing 403 may be a user interface button selectable by the user.

After a user selects a tick or other arthropod using the identify tick selection screen 400, the user may be presented with a user interface 500 to optionally add a photo of the tick or other arthropod as illustrated in FIG. 5. The user interface 500 may comprise a user interface button 503 which may open a camera application on the mobile device or may open a photo library application on the mobile device. If the user does not seek to include a photo, the user interface 500 may include a skip button 506 to allow the user to avoid including a photo.

After adding a photo or skipping the photo selection process, the user may be presented with a geolocation user interface 600. A geolocation user interface 600 may include a map 603. Using the map 603, the user may be able to mark the geographical location around which the tick was spotted. The geographical location around which the tick was spotted may be indicated by a tick flag icon 606. The user's present location may also be labeled with an icon 609. After selecting a geographical location of the sighted tick, the user may proceed by pressing a next user interface button 612.

After information relating to the sighted tick is entered into the user interface, the user may be presented with a confirmation user interface 700 confirming the user that the tick or other arthropod information has been uploaded to the database. The user may also be presented with an option to share the sighting and/or the application with users such as via social media using a share button 703.

The remove tick user interface button 315 illustrated in FIG. 3 may begin a process of recording tick information for a user who has been bitten by a tick. Upon clicking or otherwise activating the remove tick user interface button 315 illustrated in FIG. 3, the user may be presented with instructions on removing a tick as illustrated by the user interface 800 in FIG. 8. The tick removal instruction user interface 800 may include a next button 803 for the user to proceed with the process.

After the user executes the next button 803, the mobile client 112 may begin to execute a tick sighting function and the user may be presented with an identify tick selection screen 900 as illustrated in FIG. 9A.

An identify tick selection screen 900 may comprise illustrative drawings 903 or photographs of ticks and/or other arthropods. The illustrative drawings 903 may be aimed at helping an uninformed user of the application to identify the type of tick found in the wild. Each illustrative drawing may be of a specific type of tick or other arthropod or may comprise a "cannot identify" selection option. Each illustrative drawing 903 may be a user interface button selectable by the user. Upon clicking an illustrative drawing 903, the user may be presented with additional information relating to the arthropod illustrated in a user interface 950 as illustrated in FIG. 9B. The additional information may comprise a larger drawing 962 of the tick or other arthropod, a scientific name, a common name, common or known locations of the tick or other arthropod, a map 959 of common or known locations of the tick or other arthropod or other relevant information. The user interface 950 may include a back or close button 953 allowing the user to return to the identify tick selection screen 900 as illustrated in FIG. 9A. The user interface 950 may include a next button 956 allowing the user to proceed after selecting the tick or other arthropod.

After the tick identification process, the user may be presented with a geolocation user interface 1000. A geolocation user interface 1000 may include a map 1003. Using the map 1003, the user may be able to mark the geographical location around which the tick was spotted. The geographical location around which the tick was spotted may be indicated by a tick flag icon 1006. The user's present location may also be labeled with an icon 1009. After selecting a geographical location of the sighted tick, the user may proceed by pressing a next user interface button 1012.

Figure 11:
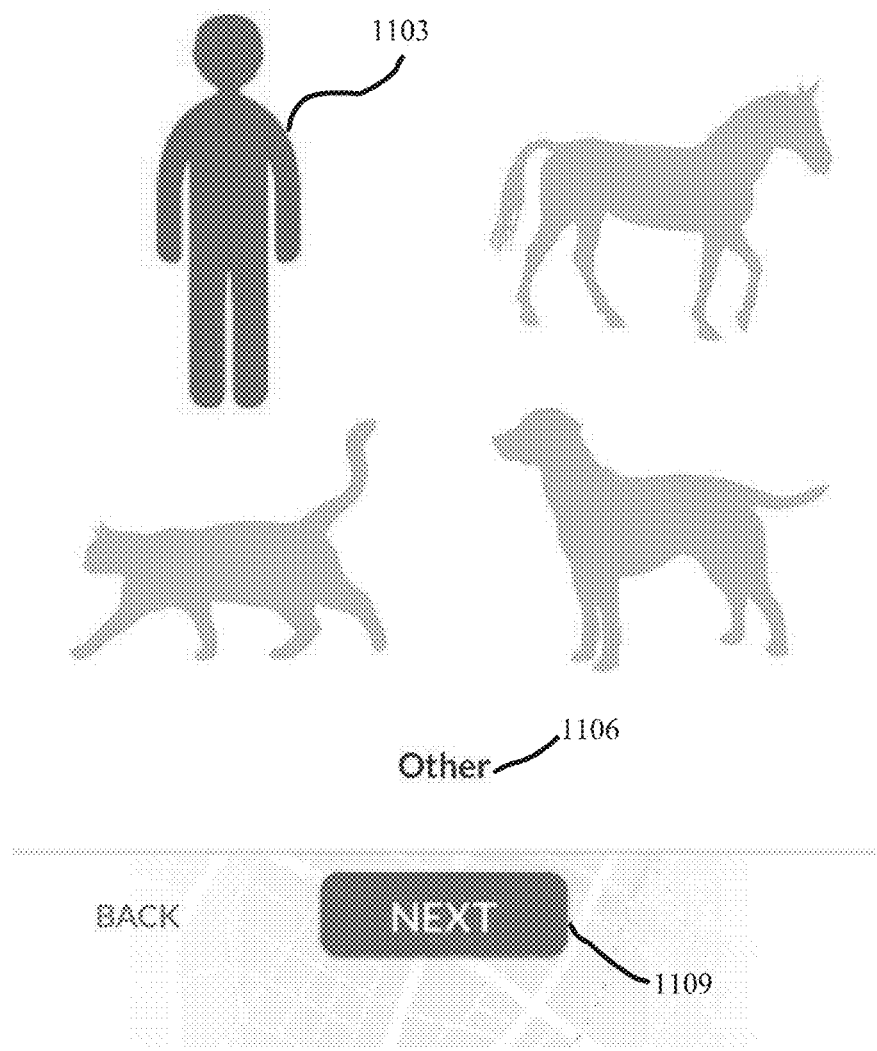
FIG. 11 illustrates a user interface allowing a user to indicate the type of potential carrier in accordance with one or more embodiments as described herein.

In some embodiments, the mobile client 112 may present a carrier identification selection user interface 1100 as illustrated in FIG. 11. Because not every tick or other arthropod bite may have been on a human, it may be important to collect information relating to what type of entity was bitten by the tick or other arthropod. For example, the carrier identification selection user interface 1100 may allow for a user to select between a human 1103, horse, cat, dog, or other arthropods by selecting between various user interface buttons. Another user interface button 1106 may be provided to select a carrier that is not depicted on the user interface 1100. After selecting a carrier in the user interface 1100, the user may select a next user interface button 1109 to continue to the next step.

Figure 12:
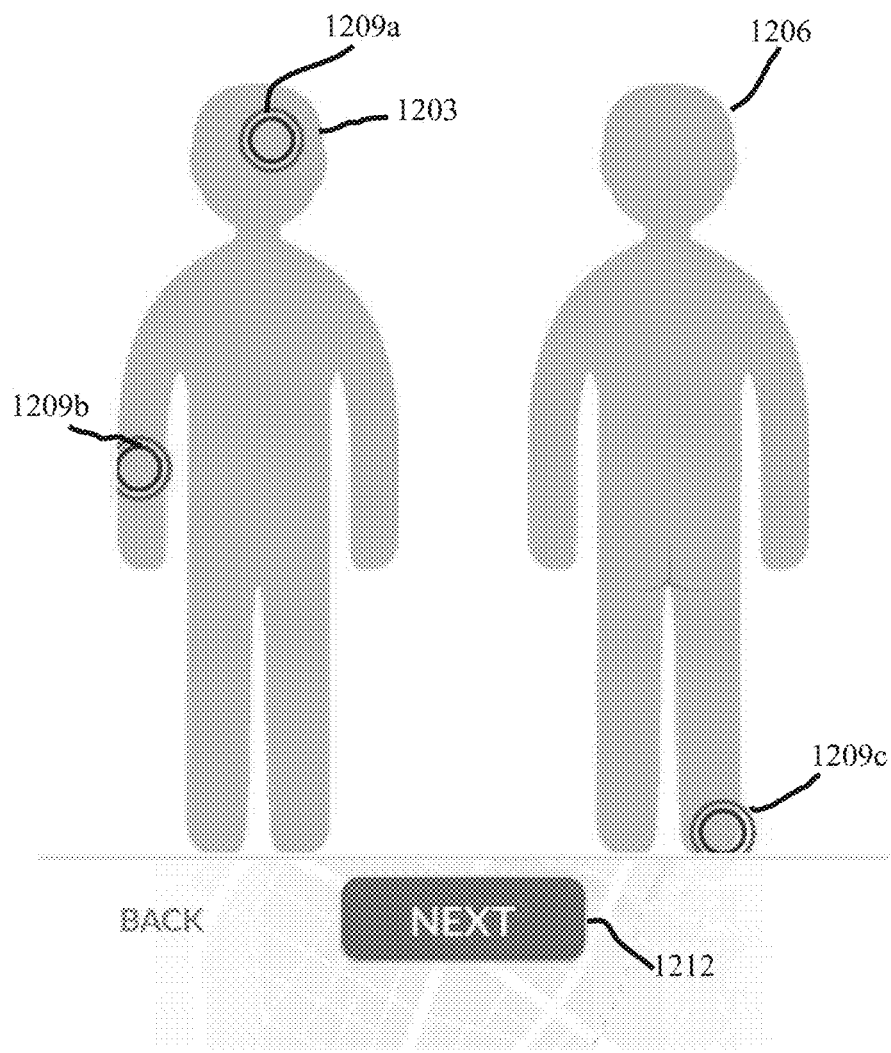
FIG. 12 illustrates a user interface allowing a user to indicate on a carrier where the arthropod bite(s) occurred in accordance with one or more embodiments as described herein.

After selecting a carrier in the user interface 1100, the user may select a location of the bite or bites using a bite location selection user interface 1200 as illustrated in FIG. 12. The bite location selection user interface 1200 may include a front outline 1203 and a rear outline 1206 of the carrier selected in the user interface 1100. A user may use the front outline 1203 and rear outline 1206 of the carrier selected in the user interface 1100 to select one or more areas 1209*a-c* of the carrier which were bitten by ticks or other arthropods. After selecting one or more areas 1209*a-c* of the carrier which were bitten by ticks or other arthropods, the user may select a next user interface button 1212 to continue to a next step.

After selecting one or more areas 1209*a-c* of the carrier which were bitten by ticks or other arthropods, the user may be presented with a bite photo upload user interface 1300. The bite photo upload user interface 1300 may include a different bite photo selection option 1303, 1309 for each of the bite locations selected in the bite location selection user interface 1200. For each bite photo selection option 1303, 1309, the bite photo upload user interface 1300 may include a take photo option 1306 or an upload photo option. After taking, selecting, or otherwise uploading a photo of each bite, the user may select a next user interface button 1312 to continue to an additional step.

Figure 14:
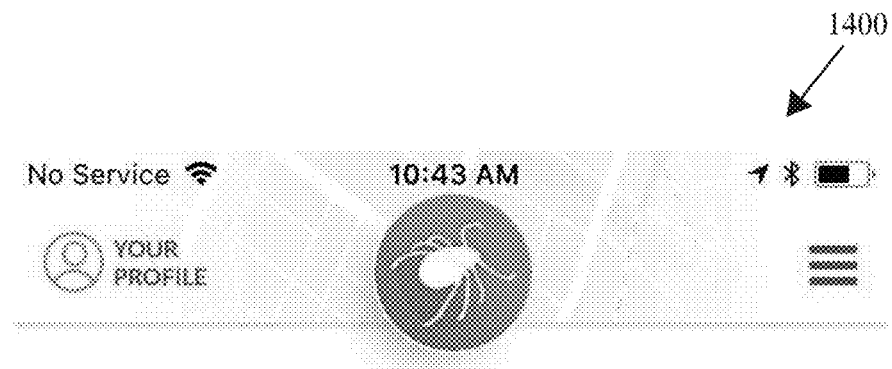
FIG. 14 illustrates a user interface allowing a user to additional information regarding the carrier and/or the biting and/or their intent of action in accordance with one or more embodiments as described herein.

The user of the mobile client 112 may also be presented with a carrier information user interface 1400 as illustrated in FIG. 14. The carrier information user interface 1400 may comprise a series of questions and/or prompts to collect information from the user relating to the tick bite and the carrier. For example, the user may be prompted with requests for information such as carrier sex, carrier age, length of time of the tick on the carrier, existence and description of any rash, symptoms, whether the carrier will get the tick tested, whether the carrier will seek medical treatment, and/or any other relevant information. After entering information in response to the requests, the user may select a next button 1403 to continue. In response, the mobile client 112 may present a user interface 1500 suggesting opportunities for the carrier to be further tested or to seek other information relating to the tick bite. Each opportunity suggestion may be accompanied by a hyperlink button 1503*a*, 1503*b* whereby the user may quickly see more information relating to each opportunity suggestion. The user may finally click a next user interface button 1506 to continue using the application.

As a user enters information relating to a tick sighting or a tick bite, the information may be uploaded to a network connected database. As different users of different devices from different locations enter additional data, new entries may be created in the database for each tick sighting and/or bite.

Figure 16:
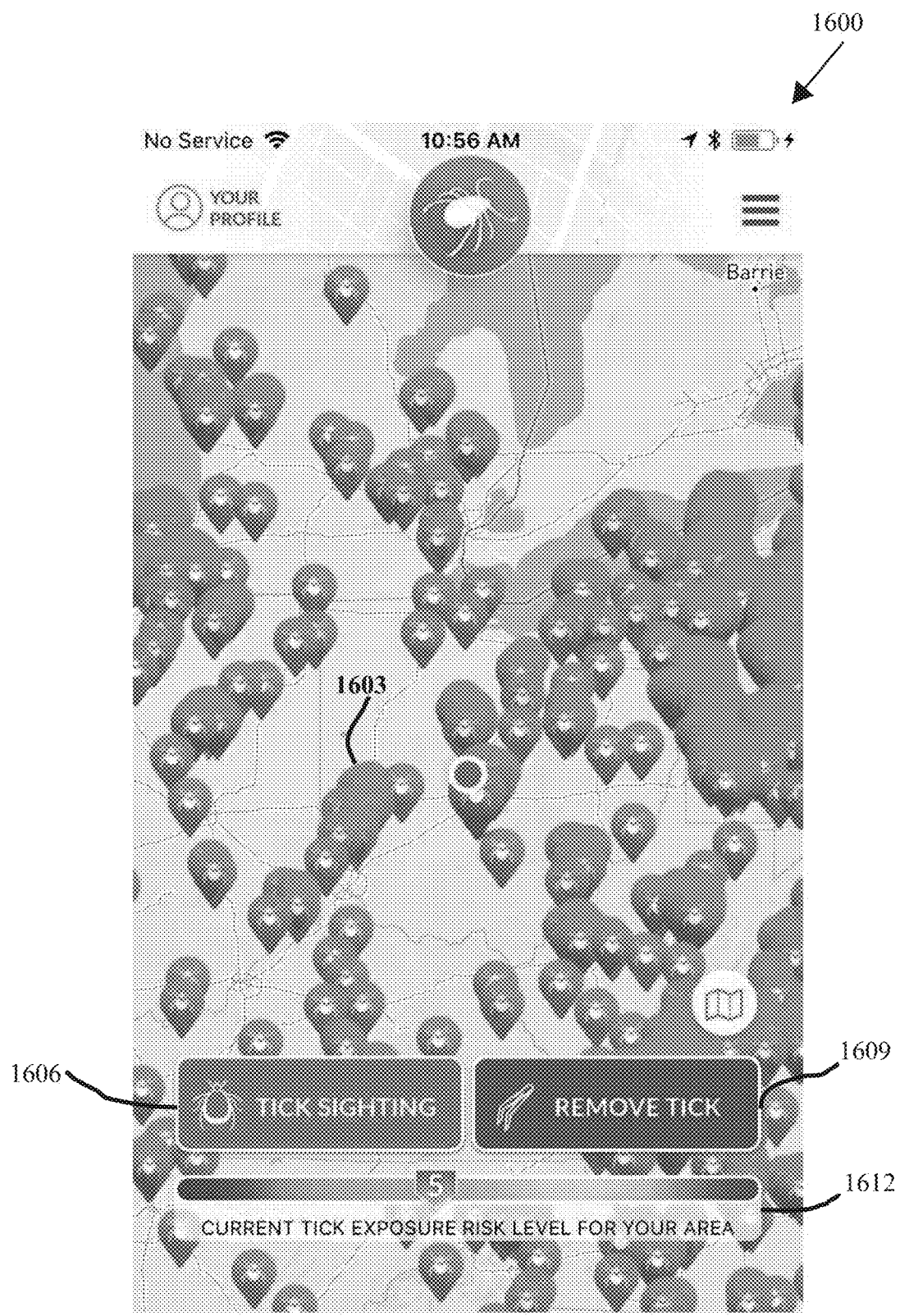
FIG. 16 illustrates a user interface providing the visualization of a geo-location-based map of various data either collected via the flows listed or data imported from approved trusted sources. It also illustrated the severity of risk of that arthropod being located within a specific geographic region to the application user in accordance with one or more embodiments as described herein.
Figure 18:
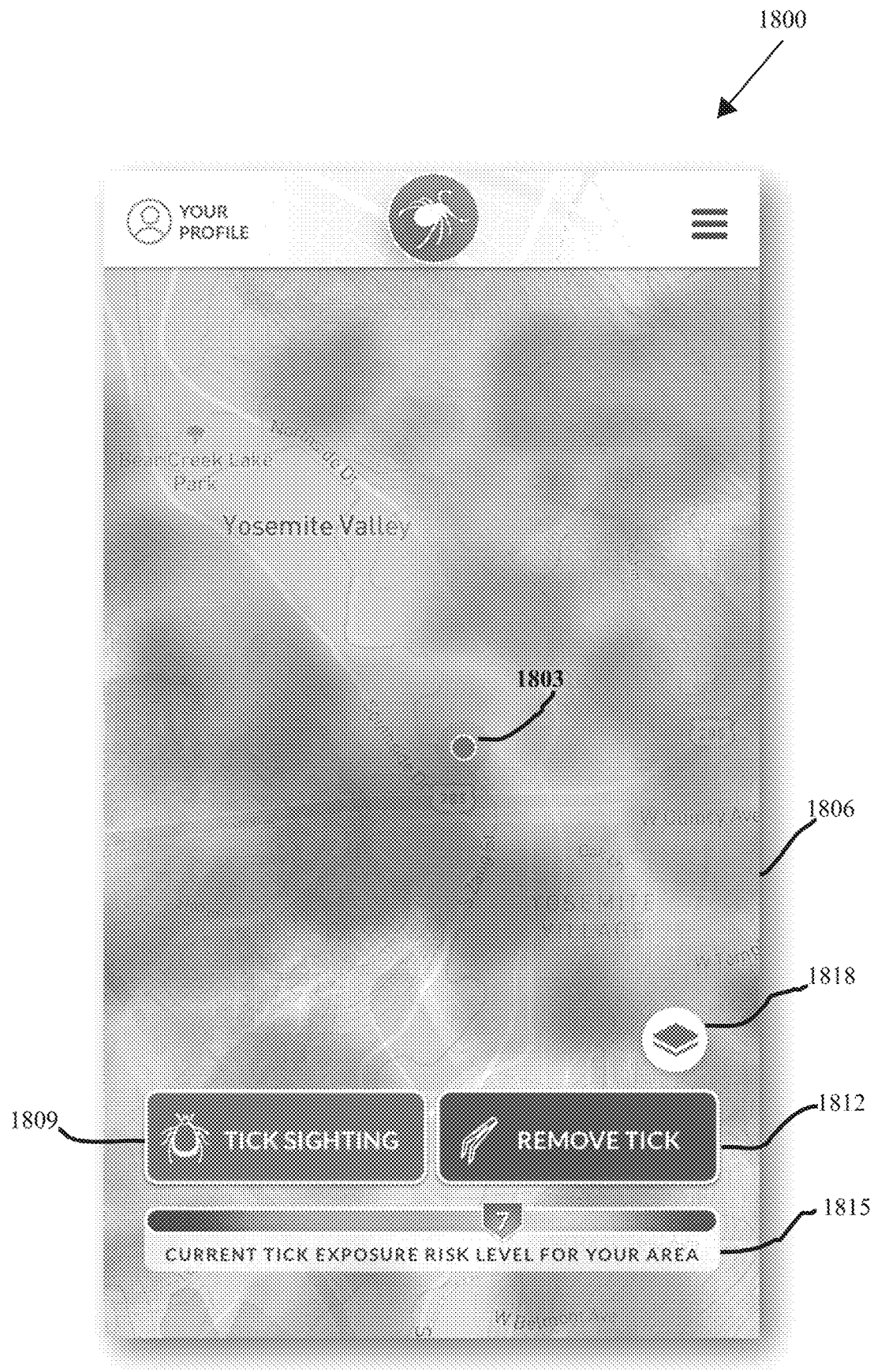
FIG. 18 illustrates a heat map user interface in accordance with one or more embodiments as described herein.

Using information from the database, the application may be able to display a map user interface 1600 as illustrated in FIG. 16. The map user interface 1600 may include a tick sighting or tick biting tag 1603 indicating each spot at which a tick was sighted or a tick was otherwise found. The map user interface 1600 may also show the user the user's current location. In some embodiments, the map user interface 1600 may load only the tick sighting tags 1603 within a certain proximity of the user's current location.

The map user interface 1600 may include a tick sighting button 1606 and/or a tick removal button 1609 which may lead the user through the above described experiences for reporting a sighting and/or a biting. The map user interface 1600 may further comprise an indication 1612 of a current tick exposure risk level for the user's area. The current tick exposure risk level for the user's area may be calculated by the application using data from the database or may be calculated by another computer system in communication with the database and the risk level may be sent to the application.

The application may include a main menu user interface 1700. The main menu user interface 1700 may include one or more options and links to features for example tick protection tips, tickborne disease resources, testing and lab resources, a link to share the application with other users, a donate button, a button to rate the application on an app store or social media, an about page providing additional information relating to the application, a game which may provide education about the risk of tick bites, a contact us page, privacy policy information, terms of use information, links to social media pages, etc.

In some embodiments, the application may be capable of displaying a tick risk heat map user interface 1800. The tick risk heat map user interface 1800 may be a layer on top of a map user interface 1600 as illustrated in FIG. 16. The tick risk heat map user interface 1800 may display a location of the user of the application with a location identification icon 1803. The tick risk heat map user interface 1800 may display a heat map layer 1806 over a map of the area of the user's location 1803. For example, red areas may represent areas of a high risk level for ticks while blue areas may represent relatively low risk levels. The tick risk heat map may be generated by the user device through the application or may be retrieved by the user device through the application via a network connection with a remote computer in communication with the database. The tick risk level may be calculated through the analysis of tick sighting and/or tick bitings reported by the user and/or other users through the application and/or through the use of data from third party databases.

The risk heat map user interface 1800 may include buttons for reporting a new tick sighting 1809 and/or reporting a new tick biting 1812. The risk heat map user interface 1800 may also include a current tick exposure risk level for the user's area indicator 1815. The risk heat map user interface 1800 may also include a map layers button 1818.

Figure 19:
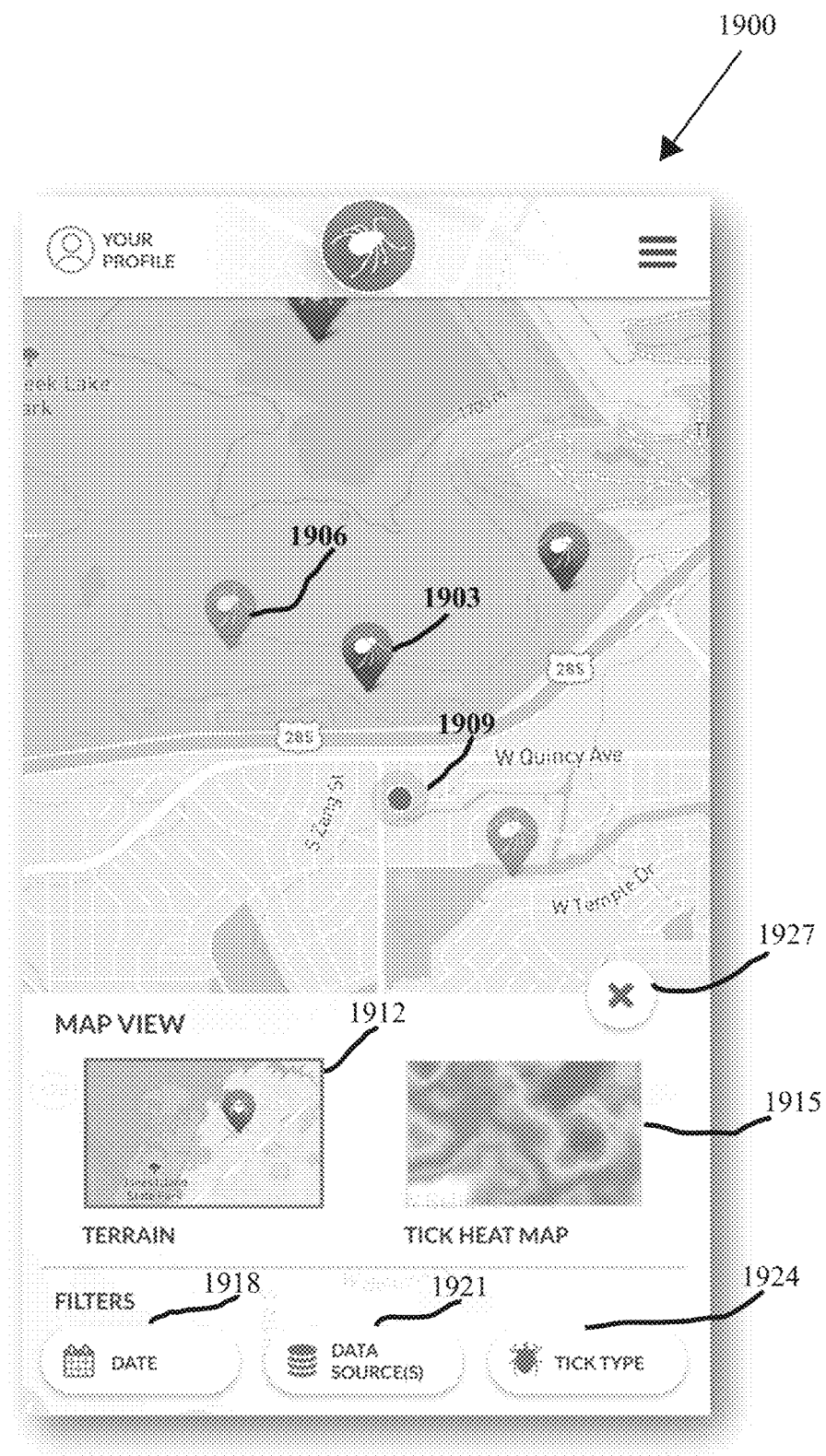
FIG. 19 illustrates a map layer user interface in accordance with one or more embodiments as described herein.

Clicking or otherwise selecting a map layers button 1818 may execute a map view option menu user interface 1900 as illustrated in FIG. 19. A map view option menu user interface 1900 may include a pop up menu window with a close button 1927. In the background, the map view option menu user interface 1900 may display a map with tick locations 1903, 1906 and a user location indicator 1909. In some embodiments, tick locations 1903, 1906 may be bold or partially transparent to show whether a tick location 1903, 1906 has a particular characteristic. For example, older tick locations 1906 may be partially transparent or a light color while newer tick locations 1903 may be bold, opaque, or a darker color to signify heightened relevance.

The map view option menu user interface 1900 may include map view options such as a terrain layer view button 1912 and/or a tick heat map layer view button 1915.

The map view option menu user interface 1900 may also include map view filters such as date 1918, data source(s) 1921, and/or tick types 1924. These map view filters may be used to limit the tick locations displayed on the map view by data relating to such filter information such as by date, by data source(s), and/or tick types.

Figures 20A, 20B, 20C:
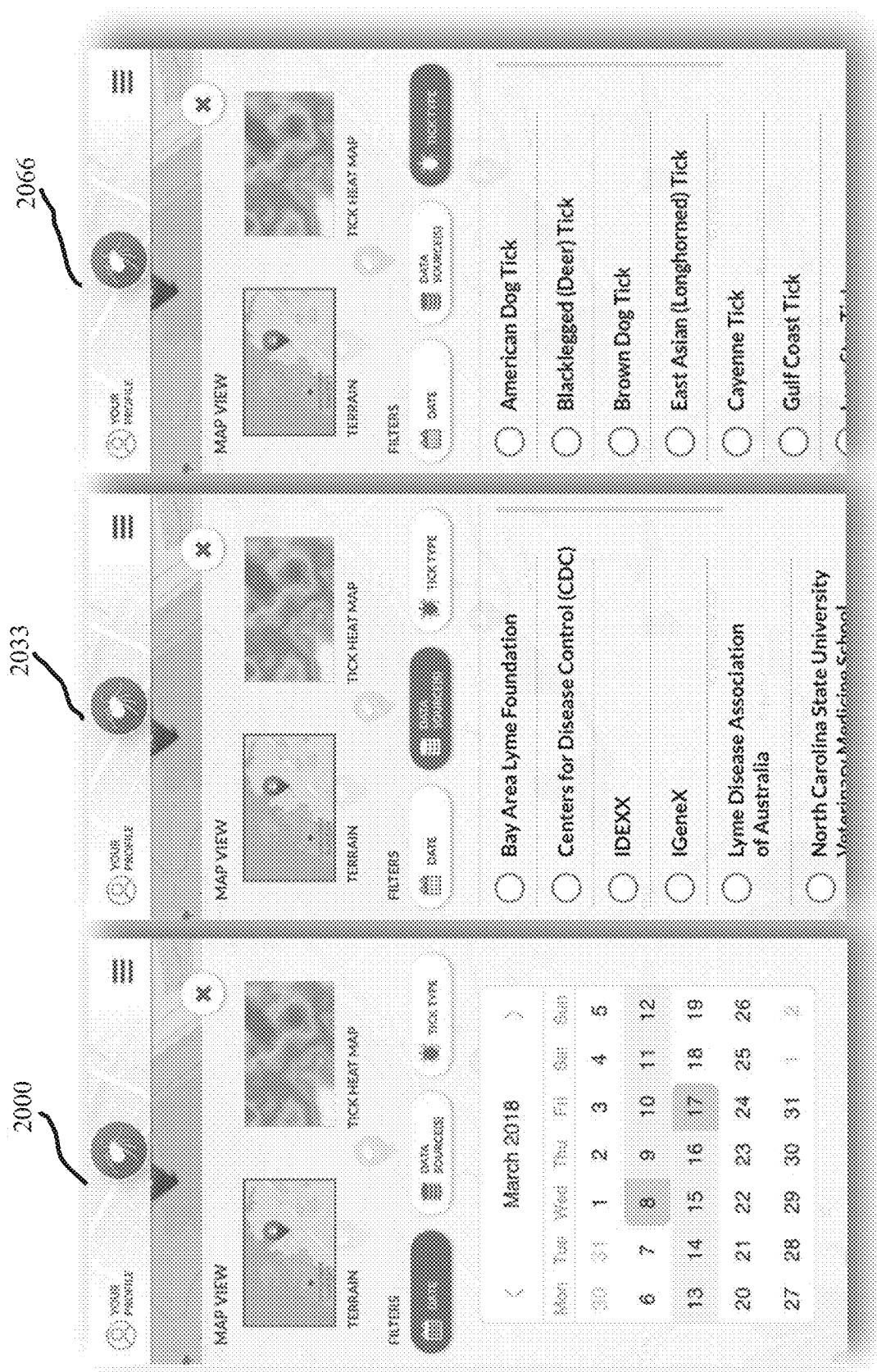
FIGS. 20A-C illustrate map layer options in accordance with one or more embodiments as described herein.

For example, as illustrated in FIG. 20A, a user may use a calendar user interface 2000 to select a date range for tick locations. After returning to the map view after selecting a date range, the map may show only those tick locations made during dates within the selected date range. For example, a user may seek to view only tick locations for a particular time in history such as on the present day in the previous year or only those tick locations/sightings in the past week or 10 days, etc.

As illustrated in FIG. 20B, a user may use a data source selector user interface 2033 to select one or more sources for the data. After returning to the map view after selecting one or more data sources, the map may show only those tick locations added by the one or more data sources. For example, a user may seek to view only tick locations from one or more data sources such as the Lyme Disease Association of Australia or the Centers for Disease Control ("CDC"). Or, a user may seek to exclude all tick locations from a particular source.

As illustrated in FIG. 20C, a user may use a tick type selector user interface 2066 to select one or more tick types. For example, a user may seek to only view locations of sighted deer ticks, or only view locations of Cayenne and Gulf Coast ticks. Or, a user may seek to exclude all sightings of one particular tick from the viewer.

The above discussed filters may be used individually or in combination to finetune a user's experience.

Figure 21C:
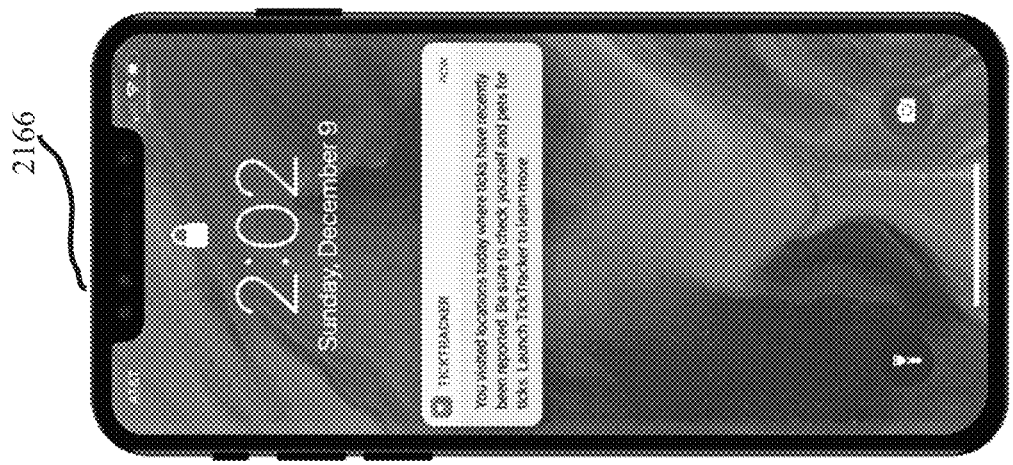
FIGS. 21A-C illustrate notifications in accordance with one or more embodiments as described herein.
Figure 21B:
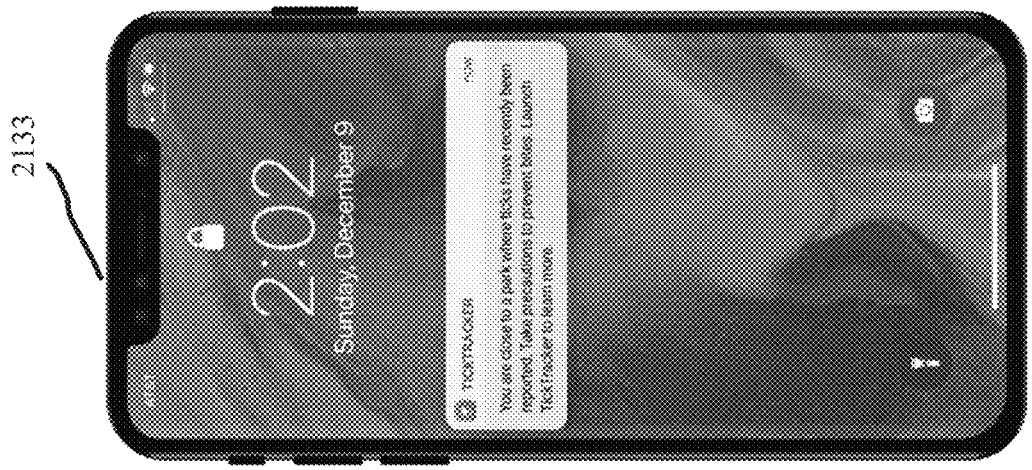
Figure 21A:
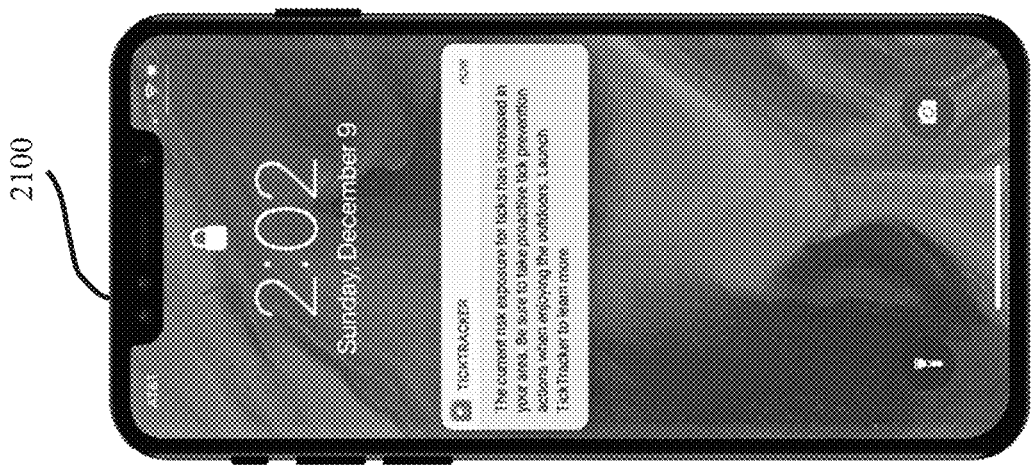

As illustrated in FIGS. 21A-C, an application as described herein may be capable of generating notifications which may be displayed on a screen of a user device executing the application. For example, an application may continuously or periodically check and update a current risk exposure for ticks in the user's area based on the location of the user device. If the application determines the current risk exposure for ticks in the user's area has increased from a risk exposure for a previous time, the application may generate a notification 2100 explaining the change to the user and providing a precautionary message related to the increased risk.

As a second example, an application may continuously or periodically check the user's location. If the application determines the user's location has become near a park or other type of area which has a relatively high or nonzero risk of ticks, the application may generate a notification 2133 explaining the risk and/or the area with the risk.

As a third example, an application may be capable of reviewing past locations of the user device. If the application determines a past location of the user device had a relatively high or nonzero risk of ticks, the application may generate a notification 2166 explaining the risk and/or the area with the risk. For example, if a user took the user device on a hiking trip into a tick-infested area and returned to a safe location, the application may determine the phone had visited the tick-infested area or an otherwise elevated tick-risk area and may generate the notification 2166. This feature may be beneficial for heightened tick-risk areas with little or no cellular service.

Figure 22:
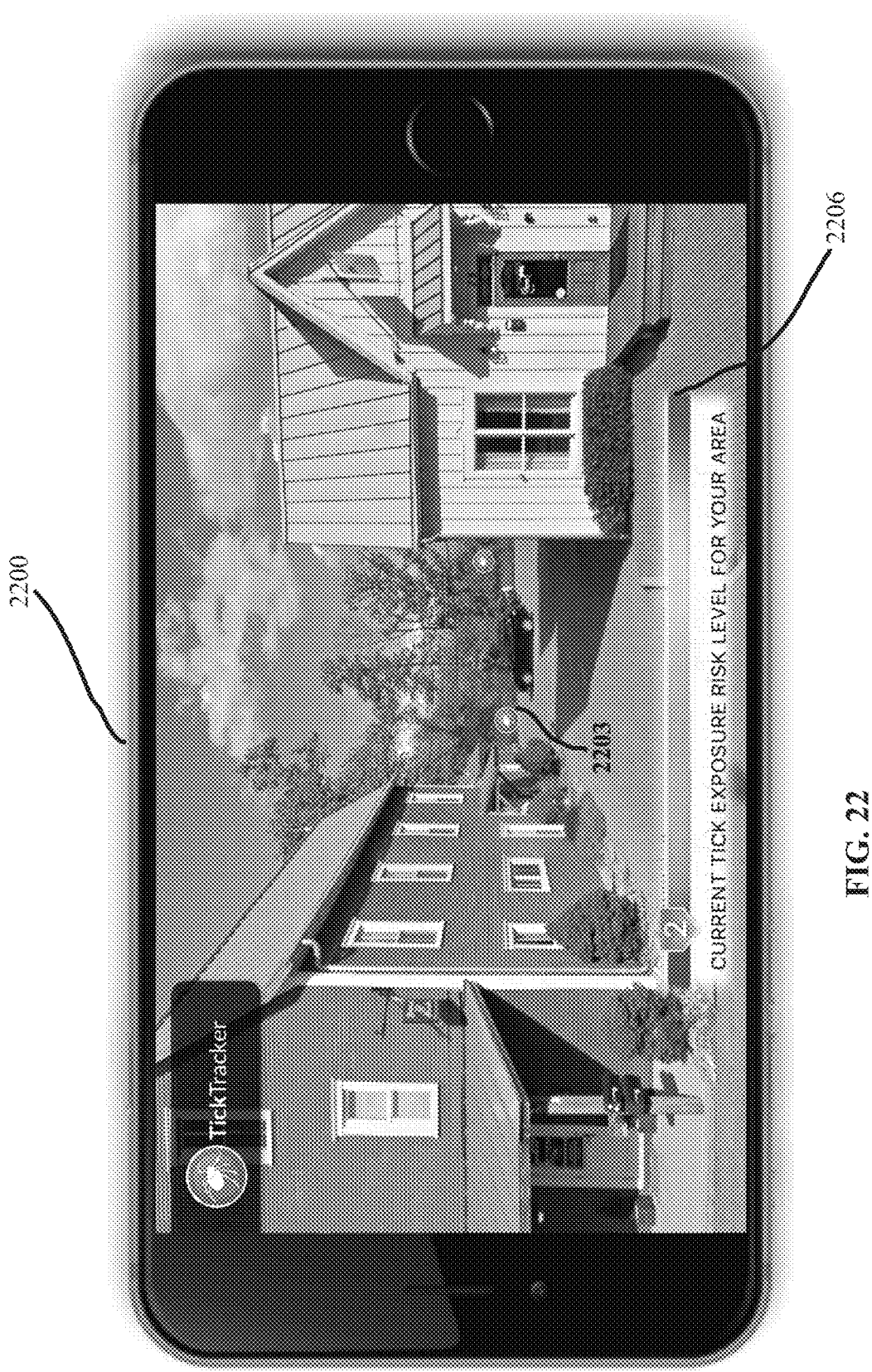
FIG. 22 illustrates an augmented reality user interface in accordance with one or more embodiments as described herein.

In some embodiments, the application may be capable of using tick-location data to generate an augmented- or virtual-reality view 2200 of the user's location with three-dimensional icons 2203 showing the locations of tick sightings and/or bitings as illustrated in FIG. 22. The augmented- or virtual-reality view 2200 may further comprise a graphical indicator 2206 showing a current tick exposure risk level for the user's area.

In some embodiments, the application may be capable of using an artificial intelligence engine to process an uploaded image of a tick and to identify a type of tick relating to the photographed tick. In some embodiments, the application may transmit the uploaded image to a network connected computer system which may perform the artificial intelligence analysis.

Figure 23:
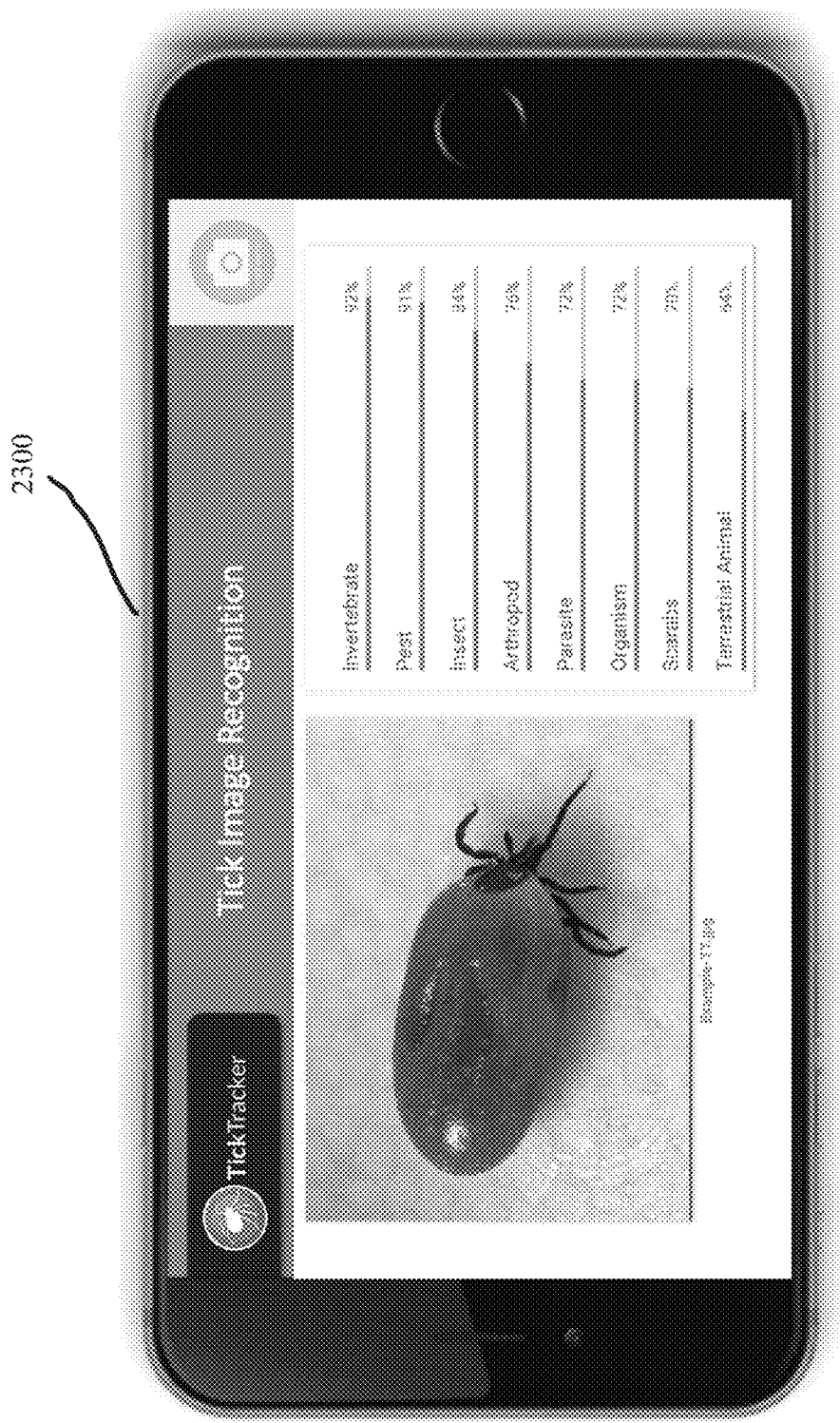
FIG. 23 illustrates an artificial intelligence tick image recognition user interface in accordance with one or more embodiments as described herein.

After the image is processed, the application may generate a tick image recognition user interface 2300 displaying the image along with a list of possibilities for the type, or other characteristics, of the imaged tick or other arthropod as illustrated in FIG. 23. Each possibility for the type or other characteristic may be presented along with an indication of the degree of confidence of the artificial intelligence engine.

Figure 24:
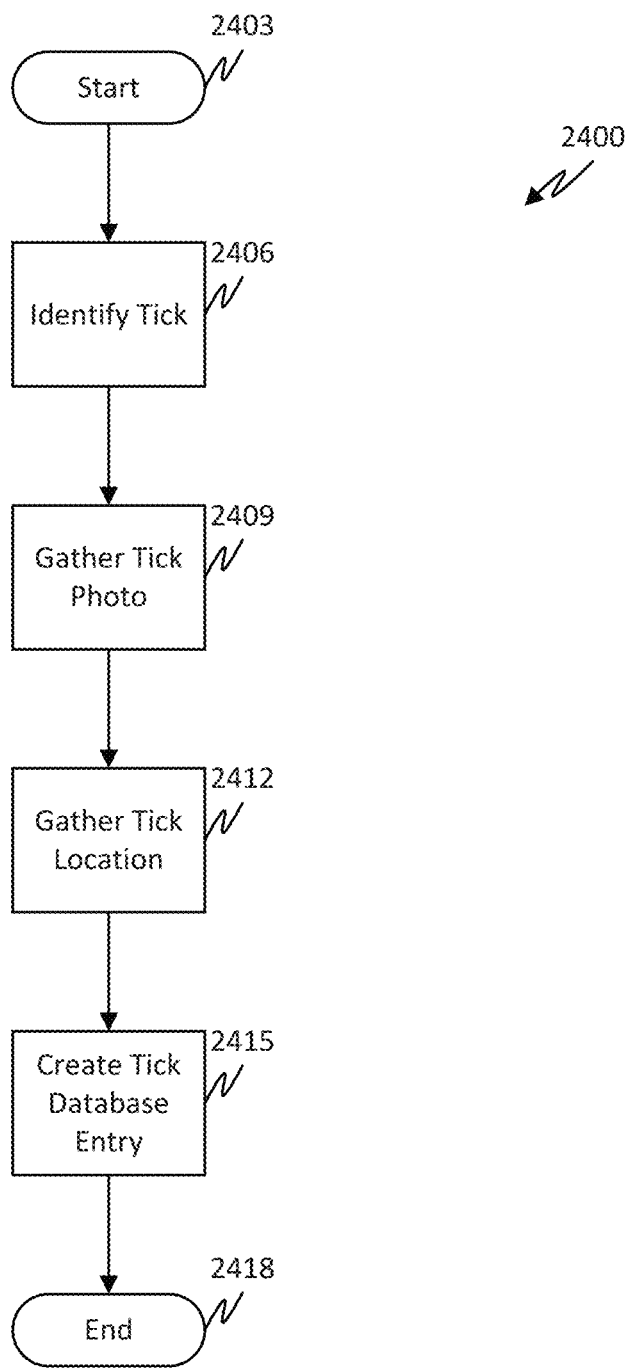
FIG. 24 is a flowchart of a method in accordance with one or more embodiments as described herein.

In some embodiments, a method 2400 of creating tick or other arthropod database entries may be performed in accordance with one or more of the elements described herein as illustrated in FIG. 24. Any of the methods described herein may be performed by a user device executing an application or by a server in communication with one or more user devices and/or one or more databases. For example, the computer system illustrated in FIG. 1A may be used to execute a tick database entry creation method.

Such a method 2400 may begin with a first step 2403. The method 2400 may in some embodiments begin with a user of an application executing on a user device touching or otherwise activating a graphical user interface button 312 in a user interface 300 such as that illustrated in FIG. 3.

Next, in step 2406, the user may be prompted to identify the type of tick or other arthropod which was located. In step 2406 the user may be presented with a user interface 400 such as that illustrated in FIG. 4 which may include graphical user interface buttons with photos of example ticks or other arthropods and may include a graphical user interface button with a none of the above or a cannot identify label.

After identifying the type of tick or other arthropod in step 2406, the method 2400 may continue with step 2409 in which the user may be prompted to gather a photograph of the tick or other arthropod. The user device may display a user interface 500 such as that illustrated in FIG. 5. The user may then use the user device to take a photograph of the tick or other arthropod or to upload an existing photograph of the tick or other arthropod.

Figure 6:
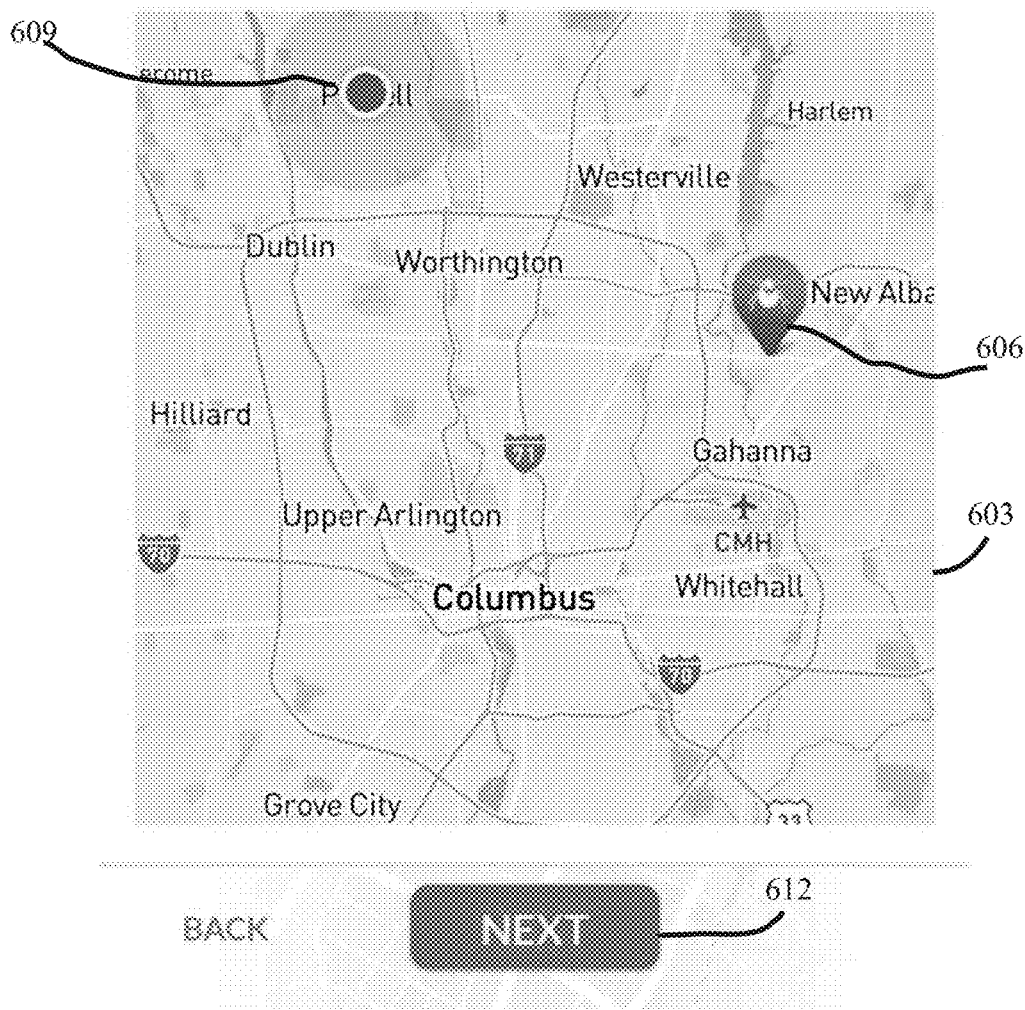
FIG. 6 illustrates a user interface allowing a user to indicate on a map where the arthropod was sighted in accordance with one or more embodiments as described herein.

Next, the user may, in step 2412, be prompted to input location information relating to the tick. For example, if the user is still at the location of the tick, the user may use the user device to record the current location. Or the user may use the user device to select a different location from the map or type in an address or other location identifying information. In some embodiments, the user may be presented with a user interface 600 such as that illustrated in FIG. 6.

Figure 7:
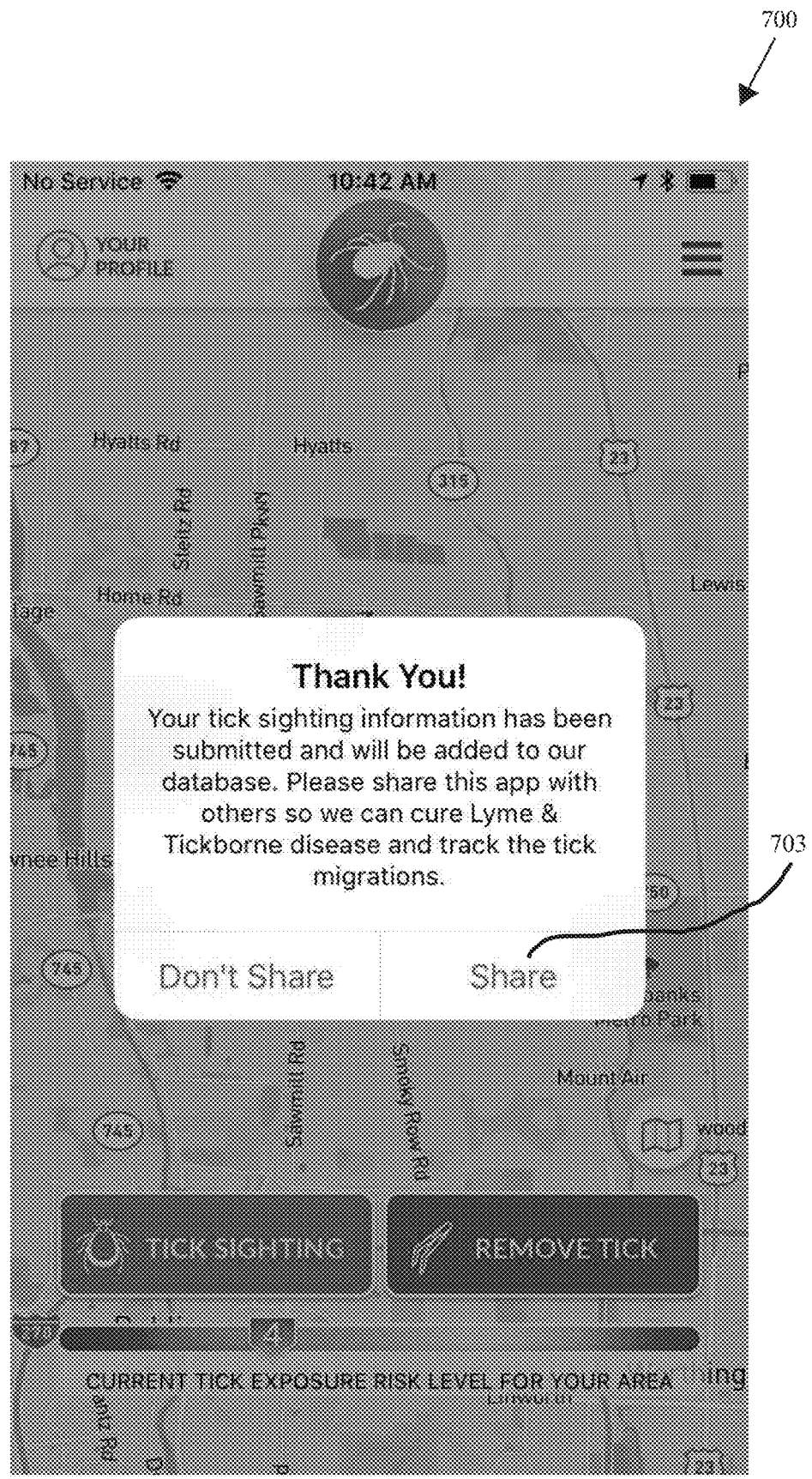
FIG. 7 illustrates a user interface allowing a user to choose whether or not to share with their peer/social networks that an arthropod sighting occurred within the application in accordance with one or more embodiments as described herein.

After inputting location information, the user may be thanked for the information such as by a user interface 700 which may be similar to that illustrated in FIG. 7. The user may also be presented with tick or other arthropod information such as precautionary steps a person can take to avoid being at risk of tick- or other arthropod-related diseases.

As the application on the user device collects the information from the user relating to the tick or other arthropod sighting, the application may transmit such information to a network location. For example, the information input by the user may be transmitted to a server executing an application designed to update and manage a database of tick or other arthropod location information. In step 2415, after obtaining the information from the user relating to the tick or other arthropod sighting, the server or another computing system may create a new entry in a database of tick or other arthropod location information. After the new database entry has been created, the method 2400 may end at step 2418.

Figure 25:
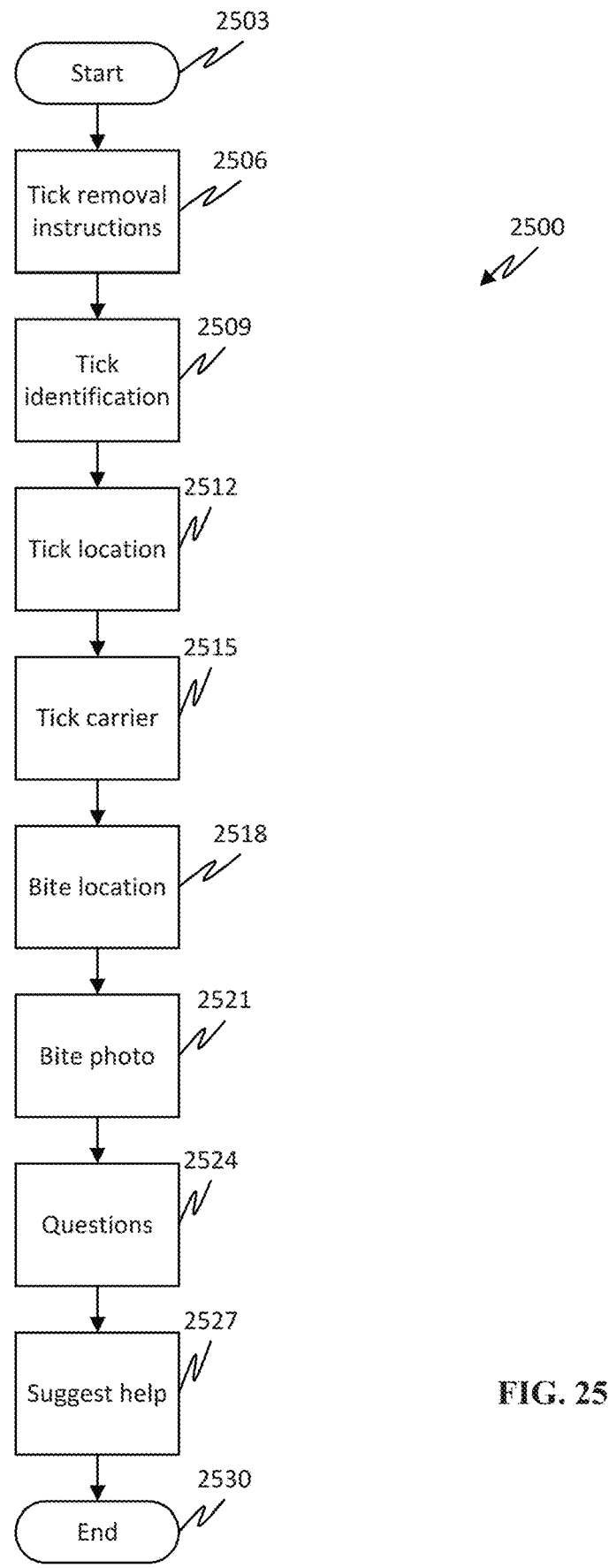
FIG. 25 is a flowchart of a method in accordance with one or more embodiments as described herein.

In some embodiments, a method 2500 of creating tick or other arthropod database entries in the event of a tick- or other arthropod-bite may be performed by a computer system in accordance with one or more of the elements described herein as illustrated in FIG. 25. Any of the methods described herein may be performed by a user device executing an application or by a server in communication with one or more user devices and/or one or more databases. For example, the computer system illustrated in FIG. 1A may be used to execute a tick database entry creation method.

Such a method 2500 may begin with a first step 2503. The method 2500 may in some embodiments begin with a user of an application executing on a user device touching or otherwise activating a graphical user interface button 315 in a user interface 300 such as that illustrated in FIG. 3. For example, an application executing on a user device may include a button for a remove tick function to be initiated by a user who has been bitten by a tick.

In step 2506, the application may present a series of tick removal instructions. For example, the application may present a user interface as illustrated in FIG. 8. The tick removal instructions may be directed to instructing a user as to safe and efficient ways to remove a tick from the user's body and may include instructions to keep the tick as a specimen for testing.

Next, in step 2509, the user may be prompted to identify the type of tick or other arthropod which was located. In step 2509 the user may be presented with a user interface 900 such as that illustrated in FIG. 9A which may include graphical user interface buttons with photos of example ticks or other arthropods and may include a graphical user interface button with a none of the above or a cannot identify label. Users may be able to use the user interface to see additional details about a particular tick for example as illustrated in FIG. 9B.

Figure 10:
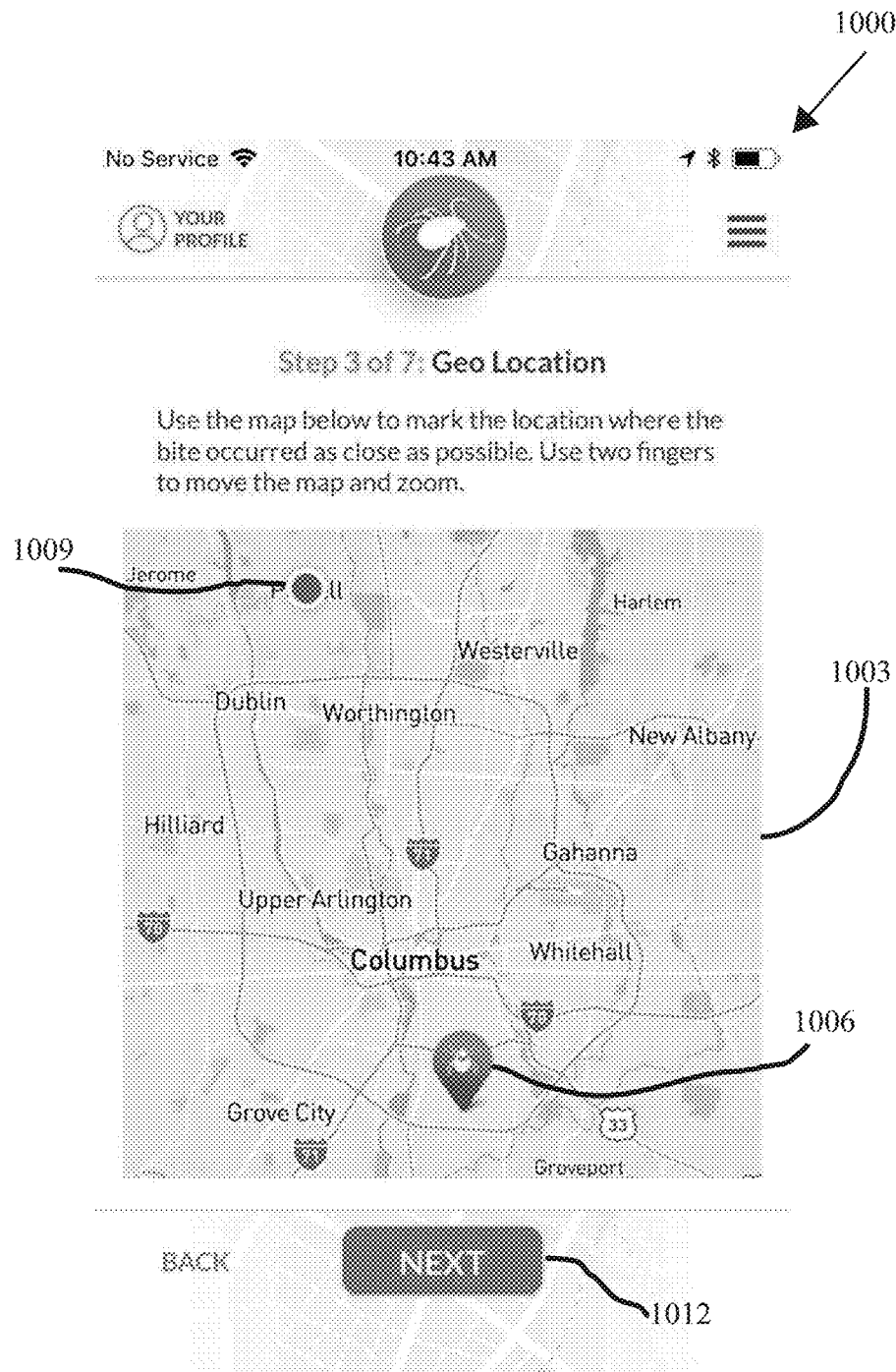
FIG. 10 illustrates a user interface allowing a user to indicate on a map where the arthropod was sighted in accordance with one or more embodiments as described herein.

Next, the user may, in step 2512, be prompted to input location information relating to the tick. For example, if the user is still at the location of the tick, the user may use the user device to record the current location. Or the user may use the user device to select a different location from the map or type in an address or other location identifying information. In some embodiments, the user may be presented with a user interface 1000 such as that illustrated in FIG. 10.

After selecting a location of the tick in step 2512, the user may be presented with a user interface to add information related to the type of carrier which was bitten by the tick in step 2515. For example, the user device executing the application may present a graphical user interface 1100 as illustrated in FIG. 11 and may include options for common carriers such as human, horse, cat, dog, or other arthropods and may include an other button for arthropods not depicted in the graphical user interface.

After selecting a carrier type in step 2515, the user device may present a menu for selecting one or more locations on the body of the carrier which were bitten by ticks in step 2518. For example, if the user chose a human in step 2515, the user interface presented may be as illustrated in FIG. 12. The user may be able to use the application to select a number of different locations to match the actual positions of the tick bites found by the user.

Figure 13:
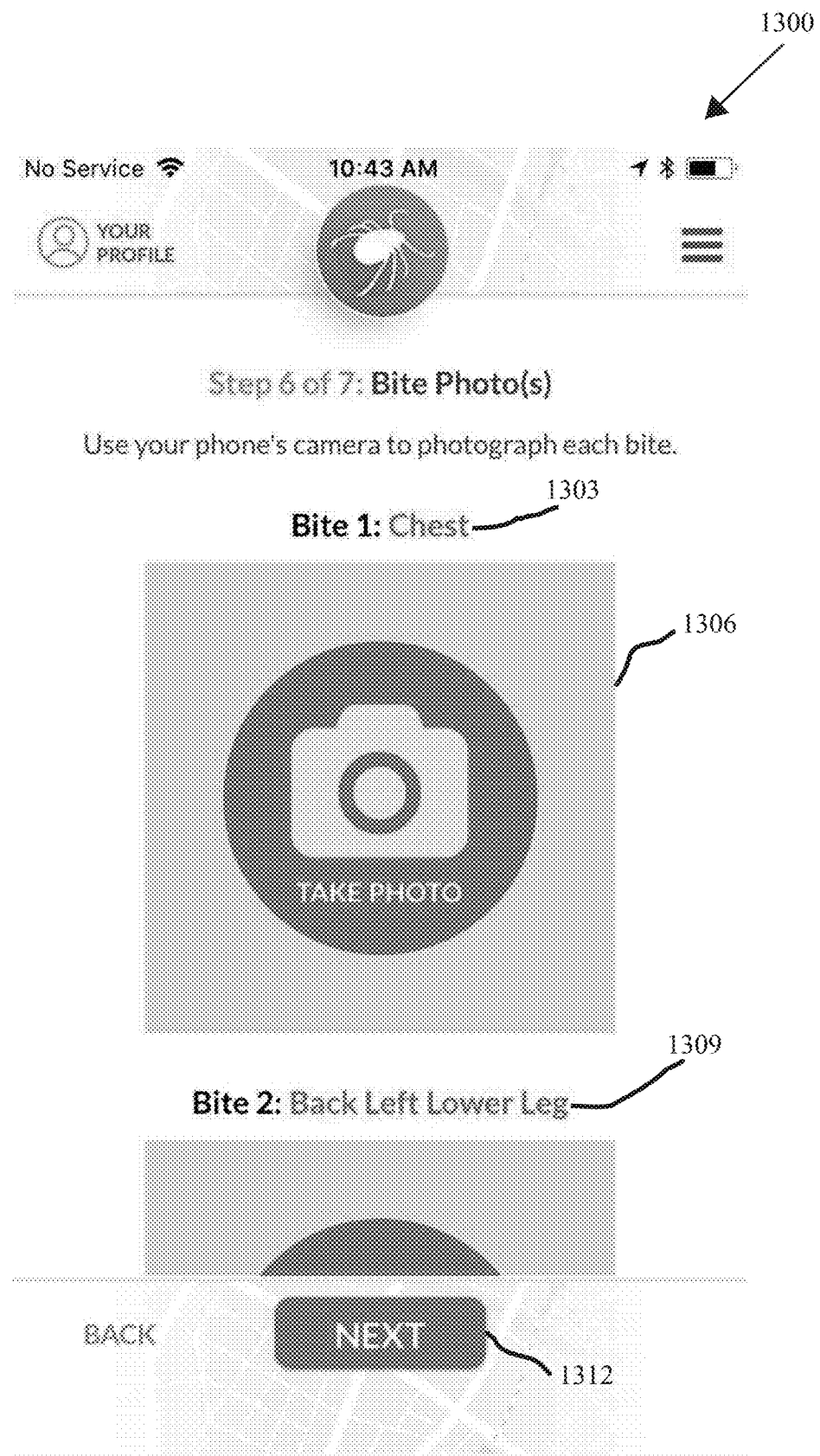
FIG. 13 illustrates a user interface allowing a user to take a picture to collect an image of the arthropod in accordance with one or more embodiments as described herein.

Next, the user may be presented with a function to add photographs of each bite in step 2521. The bite photograph selection user interface may be as illustrated in FIG. 13 and may automatically include an option for each of the locations chosen by the user in the previous step. Photographs may be uploaded by the user or the application may open a camera application to be executed on the user device. This or any other step may be optional.

Next, the user may be presented with one or more questions to provide additional information about the tick bite or bites in step 2524. For example, the application may display a user interface 1400 as illustrated by FIG. 14. Questions may include but are not limited to carrier sex, carrier age, length of time that the tick was on the carrier, the presence and type of any rash on the carrier, whether the carrier had any flu-like or other symptoms, whether the user will get the tick(s) tested, whether the carrier will seek medical treatment, etc.

Figure 15:
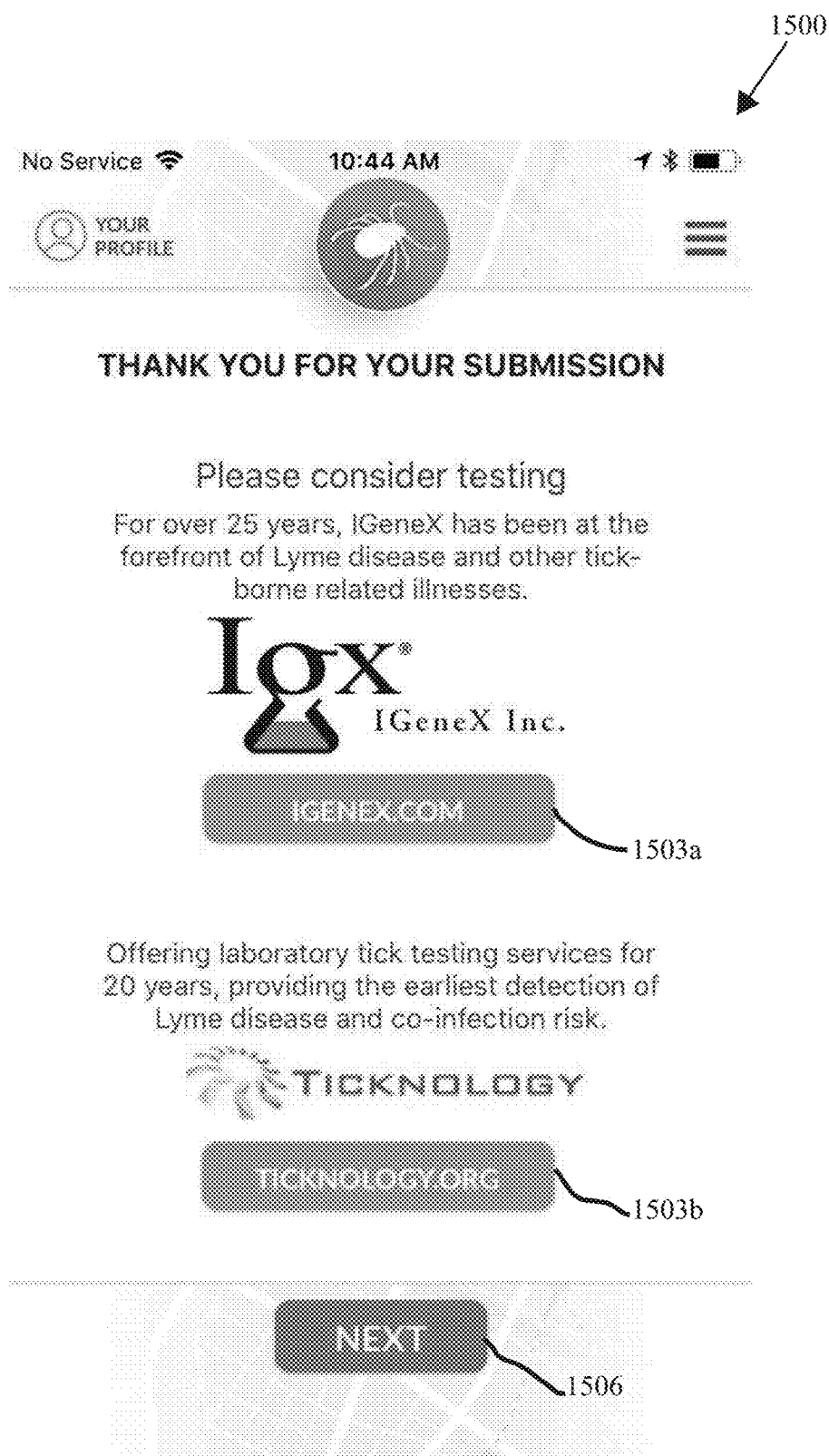
FIG. 15 illustrates a user interface allowing a user to choose a provider for getting their arthropod (i.e. Tick) tested as to whether or not the arthropod is/was a carrier of any pathogen or disease in accordance with one or more embodiments as described herein.

After the user answers questions about the tick bite or bites, the application may present another user interface to suggest testing, medical help, or other solutions in step 2527. For example, a graphical user interface 1500 as illustrated in FIG. 15 may be presented.

As the application on the user device collects the information from the user relating to the tick or other arthropod biting, the application may transmit such information to a network location. For example, the information input by the user may be transmitted to a server executing an application designed to update and manage a database of tick or other arthropod location information. After obtaining the information from the user relating to the tick or other arthropod biting, the server or another computing system may create a new entry in a database of tick or other arthropod location information. After the new database entry has been created, the method 2500 may end at step 2530.

As information is collected by an application executing on a user device, the information may be transmitted by a network connection to a network-connected computer system such as a server. The server may store such information in a network-connected database storage system.

The information may be stored as a series of entries. For example, each entry may be associated with a different tick sighting or tick bite. Each entry may include data such as photos of the tick, photos of the bite, information relating to the carrier, information relating to the area, information relating to type of tick involved, etc.

The network-connected computer system may be capable of generating a map of each tick bite or sighting entry in the database. For example, as illustrated in FIG. 16, each tick bite or sighting entry may be in the form of an icon on the map.

The network-connected computer system may also be capable of collecting relevant information from sources other than applications executing on user devices such as third party data sources for example the CDC, Lyme disease foundations, research laboratories, etc.

As new information is collected via apps and other sources, the database may be updated with new entries. Also, as additional information is collected relating to already existing entries, the network-connected computer system may be capable of updated entries. For example, if a user submitted information relating to a tick bite and later contracted Lyme disease or showed symptoms of an infection, the user may update the information using the application on the user's user device. The computer system may then take the additional information and upload the database and/or maps to show data such as confirmed diagnoses of Lyme disease, Rocky Mountain Spotted Fever, etc.

In addition to allowing users to add information relating to tick sightings and/or bites, an application may be capable of providing maps and specific location-based information for users. For example, an application may user location information to track the location of the user. The user's location may be used to obtain information relating to tick sightings and/or bitings in the area.

The application may further be capable of displaying a current risk of tick danger for the area near the user or any other area. In some embodiments, tick risk danger may be calculated by a network-based computer system such as a server. In some embodiments, tick risk danger may be calculated by an application instance executing on a user device.

Tick exposure risk levels may be calculated based on a number of factors. For example, recent tick sightings reported in the area, recent tick bitings reported in the area, seasonal data, weather data, historical data, data from third party sources, etc.

The network-based computer system may further be capable of automatically obtaining updated data from applications executing on user devices and from other sources. For example, the computer system may continuously or periodically ping user devices and network-based data sources such as third-party resources. The computer system may refresh data within the database and may check the data for accuracy. Data within the database may be associated with timestamps to be used by the computer system to check for data relevancy. The computer system may also be capable of interpreting and analyzing the data within the database.

In some embodiments, the computer system may be capable of executing one or more artificial intelligence analysis engines to analyze images uploaded with tick data.

For example, machine learning algorithms used by the computer system may be trained to recognize patterns which may be indicative of particular types of ticks or particular types of tick bites. Information gained through artificial intelligence may be used by the computer system to update entries in the database.

For example, the computer system may use artificial intelligence to review photographs of ticks uploaded by a user reporting a tick sighting. The computer system may determine through the application of the artificial intelligence engine a probable type of tick that is depicted in the photograph. Machine learning algorithms executed by the computer system may be capable of determining characteristics of a tick, such as the species of the tick, the number of legs, size, location of tick mouthparts, whether the tick is a hard or soft tick, whether the tick is an adult or nymph, age of the tick, or other information. Any information collected through such machine learning algorithms may be stored by the computer system along with the photograph of the tick.

The computer system may also use artificial intelligence to analyze photographs of tick bites. For example, an artificial intelligence engine may be trained to identify tick bite marks which are indicative of Lyme disease or any other type of infection. The computer system may be capable of executing machine learning algorithms to detect information such as size of bite mark, color of rash, particular shape of the bite mark, whether there is a ring around the bite, or other information. Any information collected through such machine learning algorithms may be stored by the computer system along with the photograph of the tick bite.

After generating new information through the analysis of photographs with the use of machine learning algorithms and/or artificial intelligence engines, new data may be added to an entry. This data may be used in a number of ways. For example, if it is determined that a bite mark in a photograph of an entry is indicative of an infection such as Lyme disease, the user associated with the entry may be notified through the application on the user's user device and may be prompted to seek medical help.

Similarly, if a photograph of a tick associated with an entry is analyzed and determined to contain a specific type of tick, the type of tick may be recorded in the entry. If the tick is a troublesome species, for example a possible carrier of a disease, the user associated with the entry may be notified and may be prompted to seek medical help.

Using the methods and systems as described herein, a solution to contemporary methods of tick-risk may be established. Such a solution may leverage crowd-sourced data in real-time utilizing mobile computer communication capabilities to enable hikers and other people to enjoy the outdoors with the comforting knowledge whether ticks or other disease-carrying arthropods are an issue for which should be prepared. Contemporary methods of tick risk calculation rely on historical data, inaccurate word of mouth, and often incorrect assumptions. Contemporary methods of collecting tick data generally involved misidentified ticks due to the period of time between a bite or sighting and the reporting. With the methods and systems presented herein, ticks can be accurately identified, quickly reported, and tick data can be quickly distributed to those potentially affected in the field.

The computer system in communication with the database may be capable of determining a tick-risk level for geographical locations of various sizes based both on actual reports from applications as well as data from third-party resources.

The tick-risk level may be an estimate of a possibility that a user in a particular geographical location may be infected by a tick- or other arthropod-borne disease. The tick-risk level may be based on a type of tick recently found in an area, actual reports of diagnoses resulting from tick bites reported in the area, historical data related to ticks and tick-borne diseases for the area, or other information. The tick-risk level may also be based at least in part in predicted tick or other arthropod migration data. For example, if a tick is found in one particular area, the computer system may be capable of determining that another tick may likely be found in another area. Similarly, if a tick is found in one particular area, the computer system may be capable of predicting that similar ticks will be found in similar locations. Similar locations may be chosen based on landscape types, wildlife types, weather patterns, climate data, etc.

The size of the geographical area may be chosen by a user of the application or may be chosen by the computer system or the application itself. The area may be a circle or may be based on a trail or other path to be taken by the user.

As new entries are added to the database, the tick risk level for an area near the new entry location may be updated. For example, a new sighting of a deer tick may increase the tick-risk level for an area surrounding the new sighting. Similarly, as older entries age, tick-risk level may be decreased without new sightings or bitings being reported.

As the tick risk level for a particular area changes, updates may be sent to users in the particular area in the form of notifications. For example, users may see notifications 2100, 2133, 2166 as illustrated in FIGS. 21A-C. To execute such a system of notification pushing, the computer system may be capable of monitoring the location of users of user devices executing the application. When a new tick sighting or biting is reported, the computer system may update tick risk levels for nearby locations. The computer system may then determine which if any users are affected. The computer system may then instruct applications executing on user devices of the affected users to generate and present notifications with information relating to the risk change.

The computer system may use geofencing analysis to determine afflicted users. In some embodiments, geofencing and user position tracking may be performed by applications executing on the user devices themselves. The application executing on the user devices may poll the computer system to check whether tick risk level for a particular area has changed and may be capable of downloading a tick risk level for that area and may then determine whether a change has occurred.

Notifications may comprise information such as whether tick-risk for the user's area has increased for example as illustrated in FIG. 21A. Such notifications may include information or a link to information as to in what ways the user may be able to reduce the risk, such as by applying arthropod repellant or by staying out of long grass.

Notifications may also be created based on a change in the user's location. For example, if a user becomes near a park or other area, the application on the user's user device may present a notification warning of the increased risk in that area.

Notifications may also be based on past locations of the user device. For example, the application may review previous location data of the user device and may determine that the user device has been in areas with increased risk data. This may be performed, for example, by the application polling the computer system for tick risk data for a number of different locations. The application executing on the user device may then determine if any of the locations had an elevated tick risk and may present a notification such as that illustrated in FIG. 21C. Such a notification may include data such as steps the user who has visited a tick infested area may take to avoid danger. For example, the notification may instruct the user to check his or her body for ticks.

In some embodiments, whether a tick risk level for a particular area warrants generating and displaying a notification may depend on the risk level. Risk levels may be, for example, a percentage or a number on a scale of one to ten. The computer system may use threshold levels to determine whether a tick risk is low, medium, or high. In some embodiments, users may be capable of setting their own threshold levels.

As discussed above, the computer system or applications may be capable of generating heat maps for areas automatically. Heatmaps may use colors to illustrate the relative tick risk for large areas. For example, red may be used to show a high level or tick risk and blue may be used to show a relatively low level of tick risk. Heat maps may be generated by the computer system and accessed by applications executing on user devices or applications executing on user devices may use database data received from the computer system to automatically generate a heatmap using processing capabilities of the user device.

For example, a computer system may generate a heat map for a particular area and may transmit such a heatmap only to users in the area. Or the computer system may generate a global heatmap and may allow any application on any user device to access the global heatmap and see a more detailed heatmap for the location of the particular area of the particular user device.

Any of the steps, functions, and operations discussed herein can be performed continuously and automatically.

The exemplary systems and methods of this disclosure have been described in relation to computer systems and mobile devices. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a method for generating arthropod-borne disease risk notifications, the method comprising: determining, by a processor of a computing device, an arthropod-borne disease risk for a location of a first user device based on data related to a plurality of arthropod locations; generating, by the processor, a notification relating to the determined arthropod-borne disease risk for the location of the first user device based on the determined arthropod-borne disease risk for the location of the first user device; receiving, by the processor, first arthropod location information from a second user device; adding, by the processor, the received first arthropod location information from the second user device to the plurality of arthropod locations; determining, by the processor, an updated arthropod-borne disease risk for the location of the first user device based on the received first arthropod location information from the second user device; automatically generating, by the processor, a notification relating to the estimated arthropod-borne disease risk for the location of the first user device based on the estimated arthropod-borne disease risk for the location of the first user device; and automatically transmitting, by the processor, the notification to the first user device.

Aspects of the above method include wherein the location of the first user device is determined by the processor prior to determining the arthropod-borne disease risk for the location of the first user device.

Aspects of the above method include wherein the data related to the plurality of arthropod locations is stored in a network-connected database.

Aspects of the above method include wherein the first arthropod location information from the second user device is entered into the second user device via a GUI of the second user device.

Aspects of the above method include wherein the data related to the plurality of arthropod locations comprises information from a plurality of third-party data sources of arthropod location information.

Aspects of the above method include wherein the first user device is capable of utilizing an augmented reality viewer to view arthropod location information from the data related to the plurality of arthropod locations.

Aspects of the above method include wherein receiving the first arthropod location information from the second user device comprises receiving a photo of an arthropod related to the first arthropod location information.

Aspects of the above method include wherein the method further comprises analyzing, by the processor, the photograph of the arthropod using an artificial intelligence engine.

Embodiments include a system, comprising: a processor; and a computer-readable storage medium storing computer-readable instructions, which when executed by the processor, cause the processor to perform: determining, by the processor, an arthropod-borne disease risk for a location of a first user device based on data related to a plurality of arthropod locations; generating, by the processor, a notification relating to the determined arthropod-borne disease risk for the location of the first user device based on the determined arthropod-borne disease risk for the location of the first user device; receiving, by the processor, first arthropod location information from a second user device; adding, by the processor, the received first arthropod location information from the second user device to the plurality of arthropod locations; determining, by the processor, an updated arthropod-borne disease risk for the location of the first user device based on the received first arthropod location information from the second user device; automatically generating, by the processor, a notification relating to the estimated arthropod-borne disease risk for the location of the first user device based on the estimated arthropod-borne disease risk for the location of the first user device; and automatically transmitting, by the processor, the notification to the first user device.

Aspects of the above system include wherein the location of the first user device is determined by the processor prior to determining the arthropod-borne disease risk for the location of the first user device.

Aspects of the above system include wherein the data related to the plurality of arthropod locations is stored in a network-connected database.

Aspects of the above system include wherein the first arthropod location information from the second user device is entered into the second user device via a GUI of the second user device.

Aspects of the above system include wherein the data related to the plurality of arthropod locations comprises information from a plurality of third-party data sources of arthropod location information.

Aspects of the above system include wherein the first user device is capable of utilizing an augmented reality viewer to view arthropod location information from data related to the plurality of arthropod locations.

Aspects of the above system include wherein receiving the first arthropod location information from the second user device comprises receiving a photo of an arthropod related to the first arthropod location information.

Aspects of the above system include wherein the system further comprises analyzing, by the processor, the photograph of the arthropod using an artificial intelligence engine.

Embodiments include a computer program product, comprising: a non-transitory computer readable storage medium having computer readable program code embodied therewith, the computer readable program code configured, when executed by a processor, to: determine an arthropod-borne disease risk for a location of a first user device based on data related to a plurality of arthropod locations; generate a notification relating to the determined arthropod-borne disease risk for the location of the first user device based on the determined arthropod-borne disease risk for the location of the first user device; receive first arthropod location information from a second user device; add the received first arthropod location information from the second user device to the plurality of arthropod locations; determine an updated arthropod-borne disease risk for the location of the first user device based on the received first arthropod location information from the second user device; automatically generate a notification relating to the estimated arthropod-borne disease risk for the location of the first user device based on the estimated arthropod-borne disease risk for the location of the first user device; and automatically transmit the notification to the first user device.

Aspects of the above computer program product include wherein the location of the first user device is determined by the processor prior to determining the arthropod-borne disease risk for the location of the first user device.

Aspects of the above computer program product include wherein the data related to the plurality of arthropod locations is stored in a network-connected database.

Aspects of the above computer program product include wherein the first arthropod location information from the second user device is entered into the second user device via a GUI of the second user device.

Embodiments include a system for generating arthropod-borne disease risk notifications, the system comprising: a module configured to determine an arthropod-borne disease risk for a location of a first user device based on data related to a plurality of arthropod locations; a module configured to generate a notification relating to the determined arthropod-borne disease risk for the location of the first user device based on the determined arthropod-borne disease risk for the location of the first user device; a module configured to receive first arthropod location information from a second user device; a module configured to add the received first arthropod location information from the second user device to the plurality of arthropod locations; a module configured to determine an updated arthropod-borne disease risk for the location of the first user device based on the received first arthropod location information from the second user device; a module configured to automatically generate a notification relating to the estimated arthropod-borne disease risk for the location of the first user device based on the estimated arthropod-borne disease risk for the location of the first user device; and a module configured to automatically transmit the notification to the first user device.

Aspects of the above system include wherein the location of the first user device is determined by the processor prior to determining the arthropod-borne disease risk for the location of the first user device.

Aspects of the above system include wherein the data related to the plurality of arthropod locations is stored in a network-connected database.

Aspects of the above system include wherein the first arthropod location information from the second user device is entered into the second user device via a GUI of the second user device.

Aspects of the above system include wherein the data related to the plurality of arthropod locations comprises information from a plurality of third-party data sources of arthropod location information.

Aspects of the above system include wherein the first user device is capable of utilizing an augmented reality viewer to view arthropod location information from the data related to the plurality of arthropod locations.

Aspects of the above system include wherein receiving the first arthropod location information from the second user device comprises receiving a photo of an arthropod related to the first arthropod location information.

Aspects of the above system include wherein the system further comprises a module configured to analyze the photograph of the arthropod using an artificial intelligence engine.

Any one or more of the aspects/embodiments as substantially disclosed herein.

Any one or more of the aspects/embodiments as substantially disclosed herein optionally in combination with any one or more other aspects/embodiments as substantially disclosed herein.

One or more means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A method for generating arthropod-borne disease risk notifications, the method comprising:
   determining, by a processor of a computing device, an arthropod-borne disease risk for a location of a first user device based on data related to a plurality of arthropod locations;
   generating, by the processor, a first notification based on the determined arthropod-borne disease risk for the location of the first user device;
   receiving, by the processor, first arthropod location information and an image from a second user device;
   processing the image from the second user device using an artificial intelligence engine;
   determining, based on the artificial intelligence engine, a type of arthropod associated with the image;
   adding, by the processor, the received first arthropod location information from the second user device and the type of arthropod associated with the image to the data related to the plurality of arthropod locations;
   updating, by the processor, the arthropod-borne disease risk for the location of the first user device based on the received first arthropod location information from the second user device and the type of arthropod associated with the image;
   after updating the arthropod-borne disease risk for the location of the first user device, determining the arthropod-borne disease risk for the location of the first user device increased; and
   in response to determining the arthropod-borne disease risk for the location of the first user device increased:
      automatically generating, by the processor, a second notification relating to the updated arthropod-borne disease risk for the location of the first user device based on the updated arthropod-borne disease risk for the location of the first user device; and
      automatically transmitting, by the processor, the second notification to the first user device.

2. The method of claim 1, further comprising determining, by the processor, the location of the first user device prior to updating the arthropod-borne disease risk for the location of the first user device.

3. The method of claim 1, further comprising storing the first arthropod location information from the second user device in a network-connected database.

4. The method of claim 1, wherein the first arthropod location information from the second user device comprises data entered into the second user device via a GUI of the second user device.

5. The method of claim 1, wherein the arthropod-borne disease risk is further determined based on information from a plurality of third-party data sources of arthropod location information.

6. The method of claim 1, further comprising utilizing an augmented reality viewer to display, on the first user device, arthropod location information based on the data related to the plurality of arthropod locations.

7. The method of claim 1, further comprising displaying, on the second user device, the image and a list of possible arthropod types associated with the image.

8. A system comprising:
   a processor; and
   a computer-readable storage medium storing computer-readable instructions, which when executed by the processor, cause the processor to:
      determine an arthropod-borne disease risk for a location of a first user device based on data related to a plurality of arthropod locations;
      generate a first notification based on the determined arthropod-borne disease risk for the location of the first user device;
      receive first arthropod location information and an image from a second user device;
      process the image from the second user device using an artificial intelligence engine;
      determine, based on the artificial intelligence engine, a type of arthropod associated with the image;
      add the received first arthropod location information from the second user device and the type of arthropod associated with the image to the data related to the plurality of arthropod locations;
      update the arthropod-borne disease risk for the location of the first user device based on the received first arthropod location information from the second user device and the type of arthropod associated with the image;

after updating the arthropod-borne disease risk for the location of the first user device, determining the arthropod-borne disease risk for the location of the first user device increased; and in response to determining the arthropod-borne disease risk for the location of the first user device increased:
automatically generate a second notification relating to the updated arthropod-borne disease risk for the location of the first user device based on the updated arthropod-borne disease risk for the location of the first user device; and
automatically transmit the second notification to the first user device.

9. The system of claim 8, wherein the instructions further cause the processor to determine the location of the first user device prior to determining the updated arthropod-borne disease risk for the location of the first user device.

10. The system of claim 8, wherein the instructions further cause the processor to store the first arthropod location information from second user device in a network-connected database.

11. The system of claim 8, wherein the first arthropod location information from the second user device comprises data entered into the second user device via a GUI of the second user device.

12. The system of claim 8, wherein the arthropod-borne disease risk is further determined based on information from a plurality of third-party data sources of arthropod location information.

13. The system of claim 9, wherein the instructions further cause the processor to utilize an augmented reality viewer to display, on the first user device, arthropod location information based on the data related to the plurality of arthropod locations.

14. A computer program product comprising:
a non-transitory computer-readable storage medium having computer-readable program code embodied therewith, the computer-readable program code configured, when executed by a processor, to:
determine an arthropod-borne disease risk for a location of a first user device based on data related to a plurality of arthropod locations;
generate a first notification based on the determined arthropod-borne disease risk for the location of the first user device;
receive first arthropod location information and an image from a second user device;
process the image from the second user device using an artificial intelligence engine;
determine, based on the artificial intelligence engine, a type of arthropod associated with the image;
add the received first arthropod location information from the second user device and the type of arthropod associated with the image to the data related to the plurality of arthropod locations;
update the arthropod-borne disease risk for the location of the first user device based on the received first arthropod location information from the second user device and the type of arthropod associated with the image;
after updating the arthropod-borne disease risk for the location of the first user device, determining the arthropod-borne disease risk for the location of the first user device increased; and
in response to determining the arthropod-borne disease risk for the location of the first user device increased:
automatically generate a second notification relating to the updated arthropod-borne disease risk for the location of the first user device based on the updated arthropod-borne disease risk for the location of the first user device; and
automatically transmit the second notification to the first user device.

15. The computer program product of claim 14, wherein the computer-readable program code is further configured to determine the location of the first user device prior to updating the arthropod-borne disease risk for the location of the first user device.

16. The computer program product of claim 14, wherein computer-readable program code is further configured to store the first arthropod location information from the second user device in a network-connected database.

17. The computer program product of claim 14, wherein the first arthropod location information from the second user device comprises data entered into the second user device via a GUI of the second user device.

18. The computer program product of claim 14, wherein the arthropod-borne disease risk is further determined based on information from a plurality of third-party data sources of arthropod location information.

19. The computer program product of claim 14, wherein the computer-readable program code is further configured to utilize an augmented reality viewer to display, on the first user device, arthropod location information based on the data related to the plurality of arthropod locations.

20. The computer program product of claim 14, wherein the computer-readable program code is further configured to display, on the second user device, the image and a list of possible arthropod types associated with the image.

* * * * *